US012123025B2

(12) United States Patent
Ben-Arye et al.

(10) Patent No.: US 12,123,025 B2
(45) Date of Patent: Oct. 22, 2024

(54) CULTURED MEAT COMPOSITIONS

(71) Applicant: ALEPH FARMS LTD., Rehovot (IL)

(72) Inventors: Tom Ben-Arye, Nesher (IL); Shulamit Levenberg, Moreshet (IL)

(73) Assignee: ALEPH FARMS LTD., Rehovot (IL)

( * ) Notice: Subject to any disclaimer, the term of this patent is extended or adjusted under 35 U.S.C. 154(b) by 238 days.

(21) Appl. No.: 16/631,217

(22) PCT Filed: Jul. 15, 2018

(86) PCT No.: PCT/IL2018/050776
§ 371 (c)(1),
(2) Date: Jan. 15, 2020

(87) PCT Pub. No.: WO2019/016795
PCT Pub. Date: Jan. 24, 2019

(65) Prior Publication Data
US 2020/0140810 A1    May 7, 2020

Related U.S. Application Data

(60) Provisional application No. 62/532,998, filed on Jul. 15, 2017.

(51) Int. Cl.
*C12N 5/071* (2010.01)
*C12N 5/00* (2006.01)
*C12N 5/077* (2010.01)

(52) U.S. Cl.
CPC ........... *C12N 5/069* (2013.01); *C12N 5/0062* (2013.01); *C12N 5/0068* (2013.01); *C12N 5/0658* (2013.01); *C12N 5/0689* (2013.01)

(58) Field of Classification Search
CPC .... C12N 5/0062; C12N 5/069; C12N 5/0658; C12N 5/0068; C12N 5/0689; C12N 2501/105; C12N 2501/11; C12N 2501/115; C12N 2502/1335; C12N 2502/1347; C12N 2533/50; C12N 5/0656; C12N 5/0659; C12N 5/0691; A23L 13/00
See application file for complete search history.

(56) References Cited

U.S. PATENT DOCUMENTS

| | | |
|---|---|---|
| 2,682,466 A | 6/1954 | Boyer |
| 3,142,571 A | 7/1964 | McAnelly |
| 3,488,770 A | 1/1970 | Atkinson |
| 3,498,794 A | 3/1970 | Calvert |
| 3,759,715 A | 9/1973 | Loepiktie |
| 3,778,522 A | 12/1973 | Strommer |
| 3,794,731 A | 2/1974 | Dannert |
| 3,814,823 A | 6/1974 | Yang |
| 3,840,679 A | 10/1974 | Liepa |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson |
| 6,835,390 B1 | 12/2004 | Vein |
| 2006/0121006 A1 | 6/2006 | Chancellor et al. |
| 2011/0091604 A1 | 4/2011 | Miller |
| 2013/0302896 A1 | 11/2013 | Shah et al. |
| 2014/0113373 A1* | 4/2014 | Chien .................... A61K 47/42 435/395 |

FOREIGN PATENT DOCUMENTS

| | | | | |
|---|---|---|---|---|
| CN | 109714962 A | * | 5/2019 | ............... A01N 1/00 |
| KR | 101851655 B1 | | 4/2018 | |
| WO | 9931222 A1 | | 6/1999 | |
| WO | 2006041429 A2 | | 4/2006 | |
| WO | 2008045506 A2 | | 4/2008 | |
| WO | 2009134197 A1 | | 11/2009 | |
| WO | 2010068897 A2 | | 6/2010 | |
| WO | 2011129756 A1 | | 10/2011 | |
| WO | 2012111000 A1 | | 8/2012 | |
| WO | 2013016547 A2 | | 1/2013 | |
| WO | 2013116446 A1 | | 8/2013 | |
| WO | 2015038988 A1 | | 3/2015 | |
| WO | 2015066377 A1 | | 5/2015 | |
| WO | 2015120174 A1 | | 8/2015 | |
| WO | 2017124100 A1 | | 7/2017 | |
| WO | 2017197138 A1 | | 11/2017 | |
| WO | 2018011805 A2 | | 1/2018 | |
| WO | 2018064968 A1 | | 4/2018 | |

(Continued)

OTHER PUBLICATIONS

Cai, Shaobo, "Electrospun Plant Protein Scaffolds with Fibers Oriented Randomly and Evenly in Three-Dimensions for Soft Tissue Engineering Applications", 2013, https://digitalcommons.unl.edu/cgi/viewcontent.cgi?article=1000&context=textilesdiss, 64 pages, pp. 1-59. (Year: 2013).*
Lab-Grown Meat: 53 Hazards Identified By FAO-Who; Apr. 24, 2023; https://meatthefacts.eu/home/activity/beyond-the-headlines/lab-grown-meat-53-hazards-identified-by-fao-who/ (Year: 2023).*
Mark J. Post; Cultured meat from stem cells: Challenges and prospects; Meat Science 92 (2012) 297-301 (Year: 2012).*
Catts and Zurr (2014) Growing for different ends. Int J Biochem Cell Biol 56: 20-29.
Du and Carlin (2012) Meat Science and Muscle Biology Symposium: extracellular matrix in skeletal muscle development and meat quality. J Anim Sci 90(3): 922-923.
Eshel et al., (2014) Land, irrigation water, greenhouse gas, and reactive nitrogen burdens of meat, eggs, and dairy production in the United States. Proc Natl Acad Sci U S A 111(33): 11996-12001.
Greger (2007) The human/animal interface: emergence and resurgence of zoonotic infectious diseases. Crit Rev Microbiol 33(4): 243-299.
Kümmerer (2003) Significance of antibiotics in the environment. J Antimicrob Chemother 52(1): 5-7.

(Continued)

*Primary Examiner* — Arthur S Leonard
*Assistant Examiner* — Masudur Rahman
(74) *Attorney, Agent, or Firm* — Rodney J. Fuller; BOOTH UDALL FULLER, PLC

(57) ABSTRACT

The invention is directed to a method for producing an edible composition, comprising incubating a three-dimensional porous scaffold and a plurality of cell types comprising: myoblasts or progenitor cells thereof, at least one type of extracellular (ECM)-secreting cell and endothelial cells or progenitor cells thereof, and inducing myoblasts differentiation into myotubes.

18 Claims, 23 Drawing Sheets

(56) References Cited

FOREIGN PATENT DOCUMENTS

| WO | 2018189738 A1 | 10/2018 | | |
|---|---|---|---|---|
| WO | 2018208628 A1 | 11/2018 | | |
| WO | WO-2018227016 A1 * | 12/2018 | ............. | A23L 13/00 |
| WO | 2019008106 A1 | 1/2019 | | |
| WO | 2019014652 A1 | 1/2019 | | |
| WO | 2019211189 A1 | 11/2019 | | |

OTHER PUBLICATIONS

Liu et al., (2016) Emergence of plasmid-mediated colistin resistance mechanism MCR-1 in animals and human beings in China: a microbiological and molecular biological study. Lancet Infect Dis 16(2): 161-168.

Loh and Choong (2013) Three-dimensional scaffolds for tissue engineering applications: role of porosity and pore size. Tissue Eng Part B Rev 19(6): 485-502.

Nishimura (2015) Role of extracellular matrix in development of skeletal muscle and postmortem aging of meat. Meat Sci 109: 48-55.

Peters et al., (2007) Testing a complete-diet model for estimating the land resource requirements of food consumption and agricultural carrying capacity: The New York State example. Renewable Agriculture and Food Systems 22(2): 145-153.

Post (2012) Cultured meat from stem cells: challenges and prospects. Meat Sci 92(3): 297-301.

Post (2014) Cultured beef: medical technology to produce food. J Sci Food Agric. Accepted article published: Nov. 9, 2013; Published online in Wiley Online Library: DOI 10.1002/jsfa.6474. 3 pages.

Schmidinger; Worldwide alternatives to animal derived foods—overview and evaluation models: solutions to global problems caused by livestock. Dissertation to obtain the doctor's degree, at the University of Natural Resources and Life Sciences, Vienna, Austria. Feb. 2012. 260 pages.

Tuomisto and de Mattos (2011) Environmental impacts of cultured meat production. Environ Sci Technol, dx.doi.org/10.1021/es200130u; 7 pages.

Velleman (1999) The role of the extracellular matrix in skeletal muscle development. Poult Sci 78(5): 778-784.

Verbeke et al., (2015) 'Would you eat cultured meat?': Consumers' reactions and attitude formation in Belgium, Portugal and the United Kingdom. Meat Sci 102: 49-58.

CDC Estimates of Foodborne Illness in the United States: CDC 2011 Estimates: Findings. Feb. 2011; 2 pages.

PCT Search Report for International Application No. PCT/IL2018/050776, mailed Oct. 21, 2018, 4 pp.

PCT Preliminary Report for International Application No. PCT/IL2018/050776, dated Jan. 21, 2020, 8 pp.

PCT Written Opinion for International Application No. PCT/IL2018/050776, mailed Oct. 21, 2018, 7 pp.

Bhat et al., (2011) Tissue engineered meat-Future meat. Journal of Stored Products and Postharvest Research 2(1): 1-10.

Noor et al., (2016) Newer trends and techniques adopted for manufacturing of In vitro meat through "tissue-engineering" technology: A review. International Journal of Biotech Trends and Technology (IJBTT) 6(4): 14-19.

Ku et al., (2014) Water-stable three-dimensional ultrafine fibrous scaffolds from keratin for cartilage tissue engineering. Langmuir 30(28): 8461-8470.

Bhat and Fayaz (2011) Prospectus of cultured meat—advancing meat alternatives. Journal of Food Science and Technology vol. 48: 125-140.

Edelman et al., (2005) Commentary: In vitro-cultured meat production. Tissue Eng 11(5-6): 659-662.

Koffler et al., (2011) Improved vascular organization enhances functional integration of engineered skeletal muscle grafts. Proc Natl Acad Sci U S A 108(36): 14789-14794.

Levenberg et al., (2005) Engineering vascularized skeletal muscle tissue. Nat Biotechnol 23(7): 879-884.

Ku et al., (2014) Intrinsically water-stable electrospun three-dimensional ultrafine fibrous soy protein scaffolds for soft tissue engineering using adipose derived mesenchymal stem cells. RSC Adv 4: 15451-15457.

Catts and Zurr (2002) Growing Semi-Living Sculptures: The Tissue Culture Art Project. Leonardo 35(4): 365-370.

Discher et al., (2009) Growth factors, matrices, and forces combine and control stem cells. Science 324(5935): 1673-1677.

Engler et al., (2006) Matrix elasticity directs stem cell lineage specification. Cell 126(4): 677-689.

Lu et al., (2013) Techniques for fabrication and construction of three-dimensional scaffolds for tissue engineering. Int J Nanomedicine 8: 337-350.

Sadovoy et al., (2014) Cellular Matrices (Scaffolds) for Bone Regeneration: State of the Art. Hir Pozvonoc (Spine Surgery) 2: 79-86. Abstract.

Toh et al., (2012) Modulation of mesenchymal stem cell chondrogenesis in a tunable hyaluronic acid hydrogel microenvironment. Biomaterials 33(15): 3835-3845. Abstract.

Verkhovskaya et al., (1990) The effect of glycerol alkoxy-derivatives on morphological and functional properties of continuous cell culture. Cryobiology 1: 30-34. Abstract.

Young and Engler (2011) Hydrogels with time-dependent material properties enhance cardiomyocyte differentiation in vitro. Biomaterials. Author manuscript; available in PMC Feb. 1, 2012. Published in final edited form as: Biomaterials. Feb. 2011; 32(4): 1002-1009.

Andersen et al., (2015) 3D Cell Culture in Alginate Hydrogels. Microarrays (Basel) 4(2): 133-161.

Chiu et al., (2012) Permeability of three-dimensional fibrin constructs corresponds to fibrinogen and thrombin concentrations. Biores Open Access 1(1): 34-40. With correction.

* cited by examiner

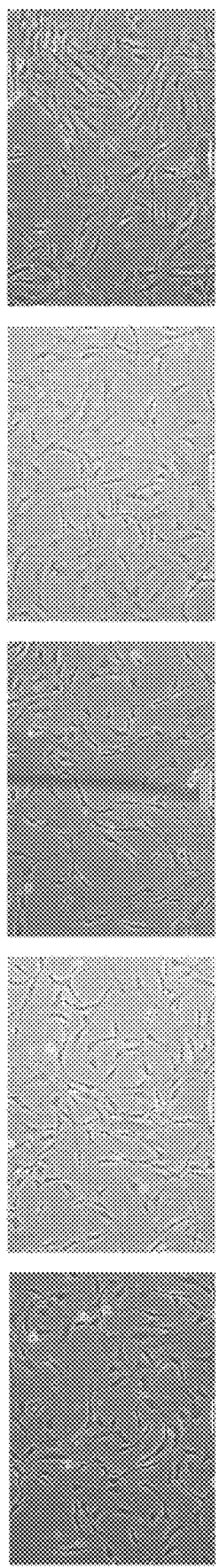
FIGURE 9A  FIGURE 9B  FIGURE 9C  FIGURE 9D  FIGURE 9E
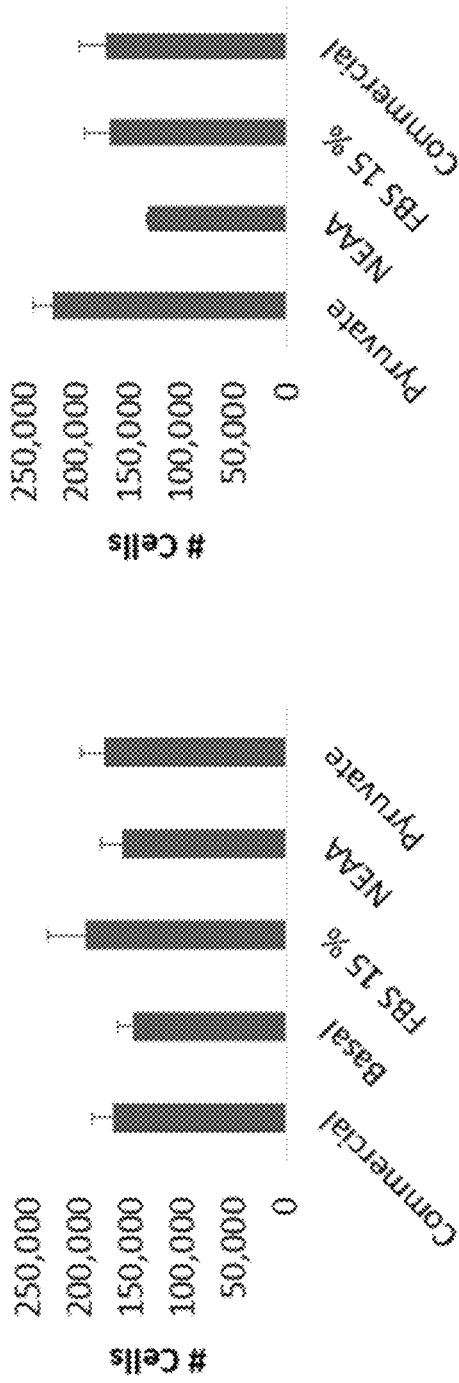
FIGURE 10A
FIGURE 10B

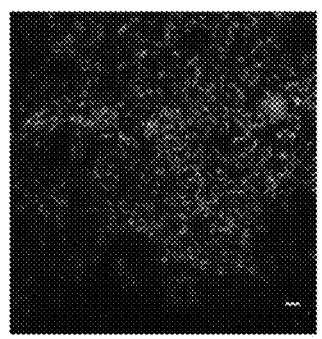 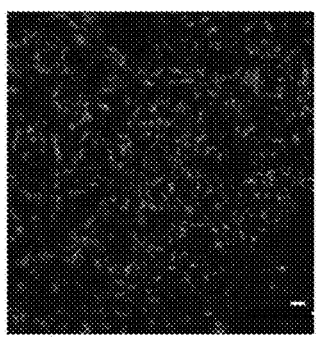 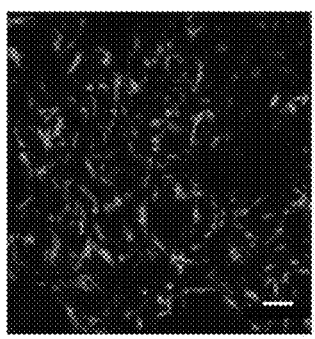
FIGURE 14A  FIGURE 14B  FIGURE 14C
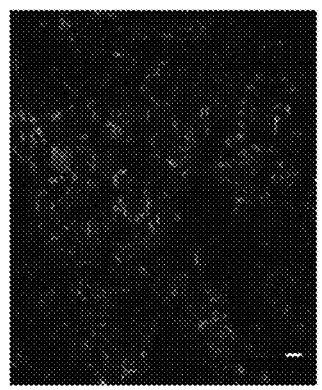  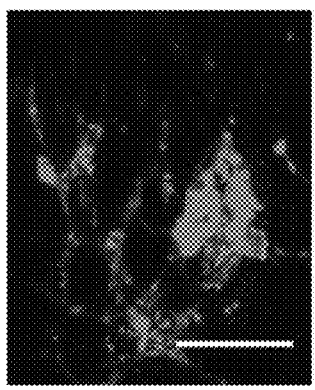
FIGURE 14D  FIGURE 14E  FIGURE 14F
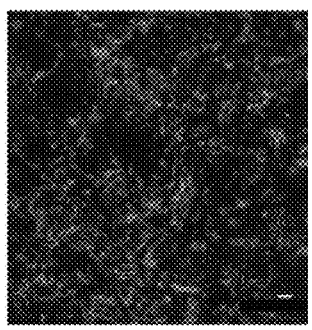 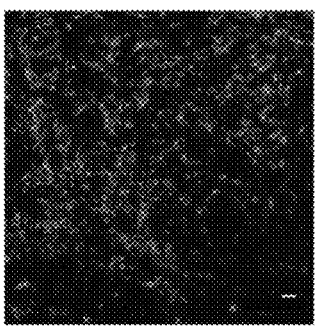
FIGURE 15A  FIGURE 15B
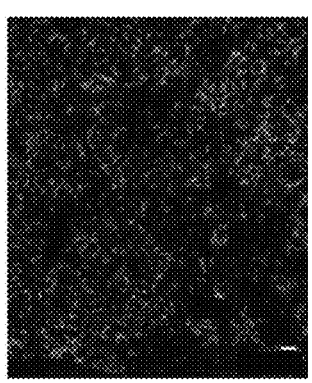 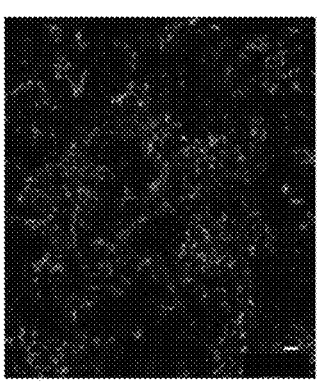 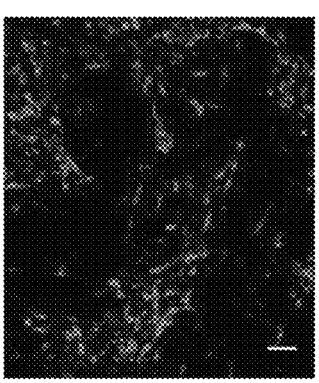
FIGURE 15C  FIGURE 15D  FIGURE 15E

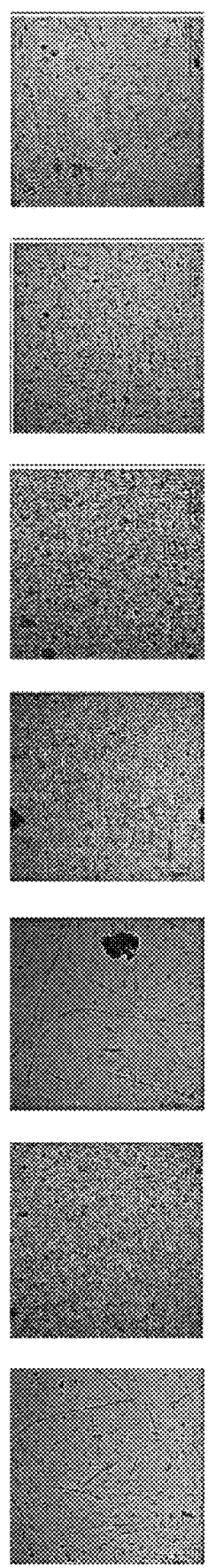
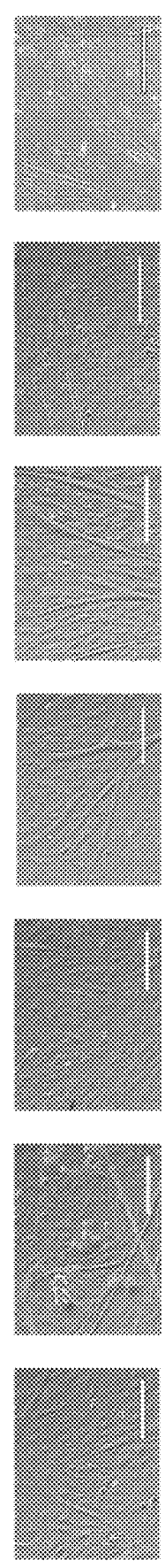
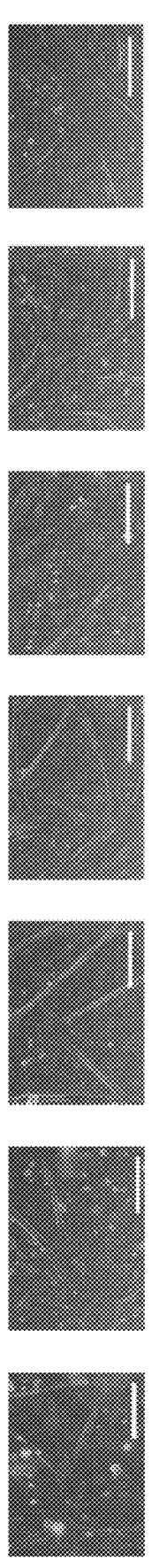
FIGURE 18A – FIGURE 18G
FIGURE 19A – FIGURE 19G
FIGURE 20A – FIGURE 20G

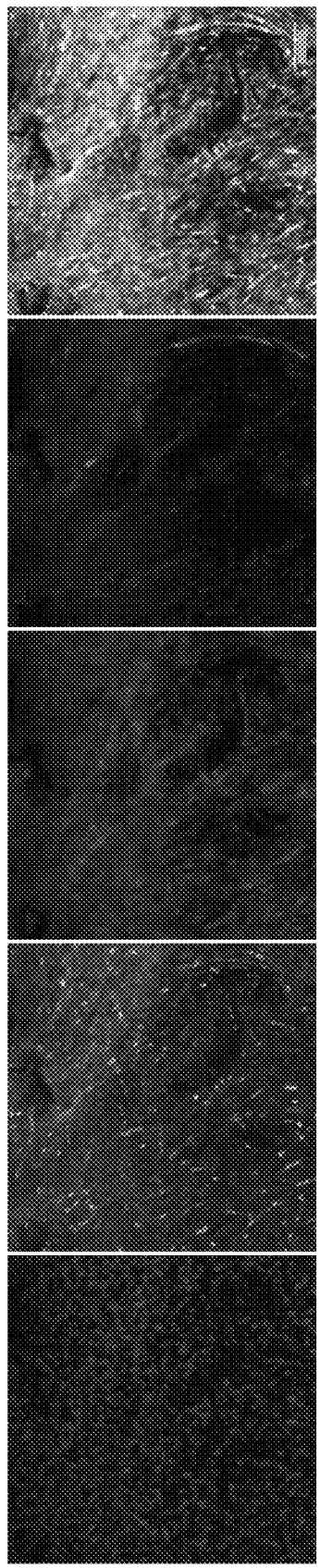
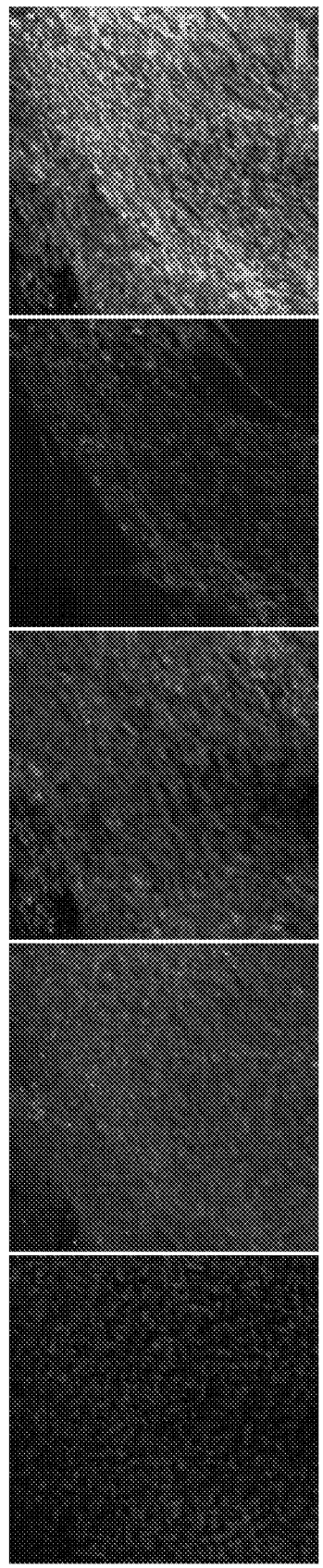
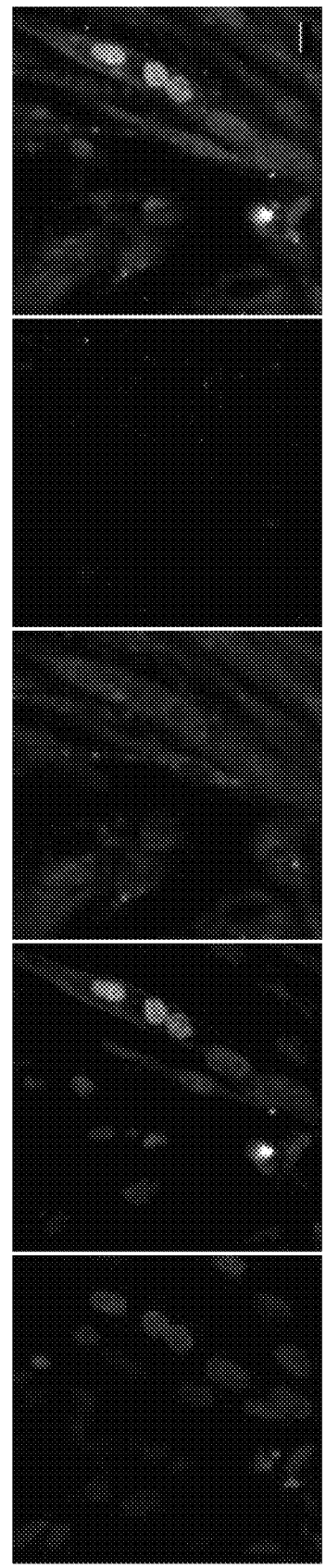

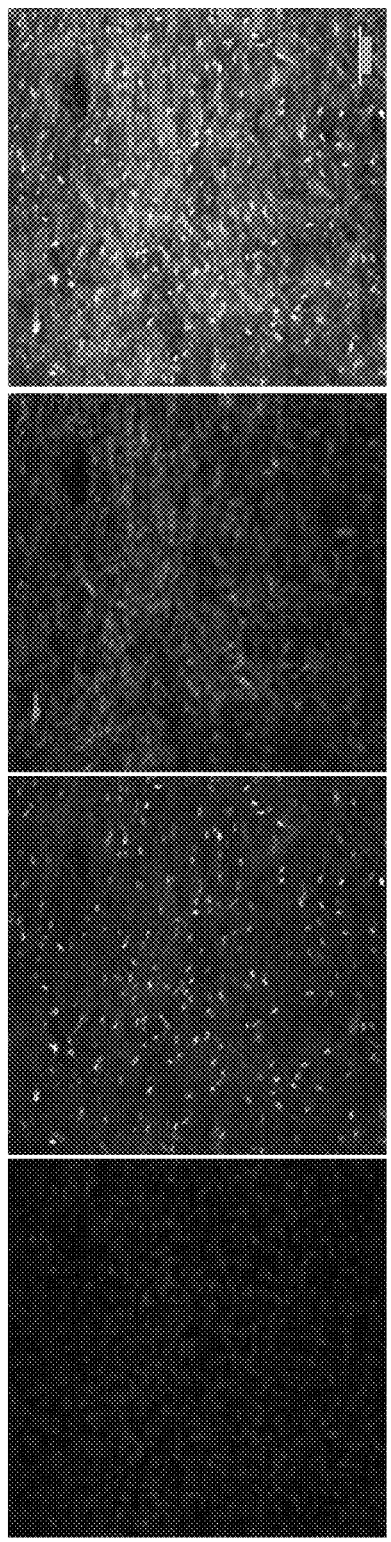
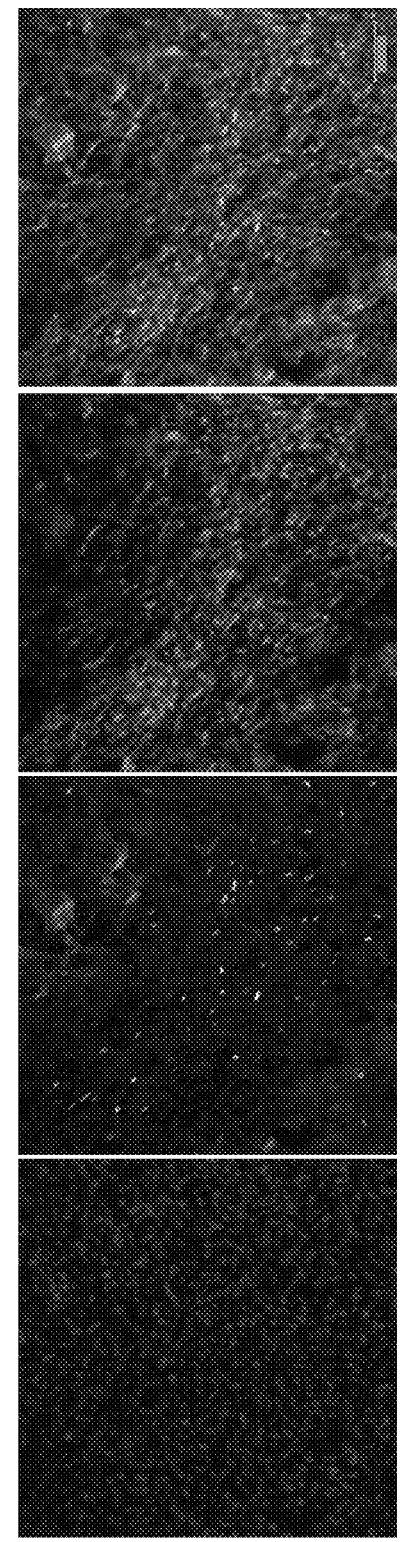
FIGURE 25A, FIGURE 25B, FIGURE 25C, FIGURE 25D, FIGURE 25E, FIGURE 25F, FIGURE 25G, FIGURE 25H

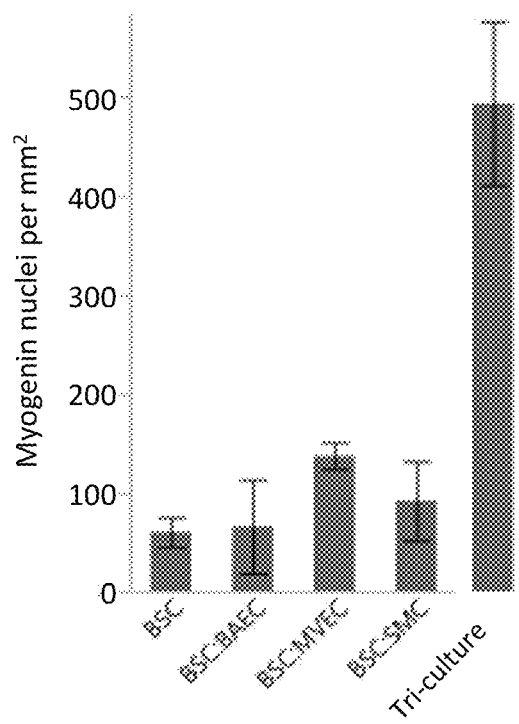
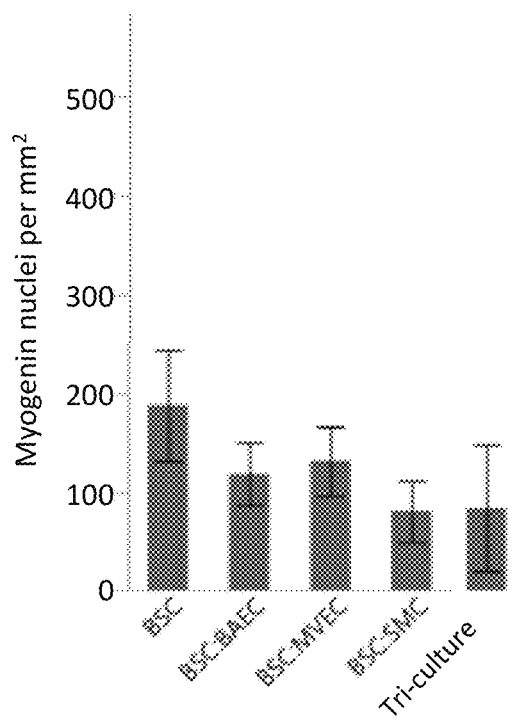
FIGURE 28A
FIGURE 28B
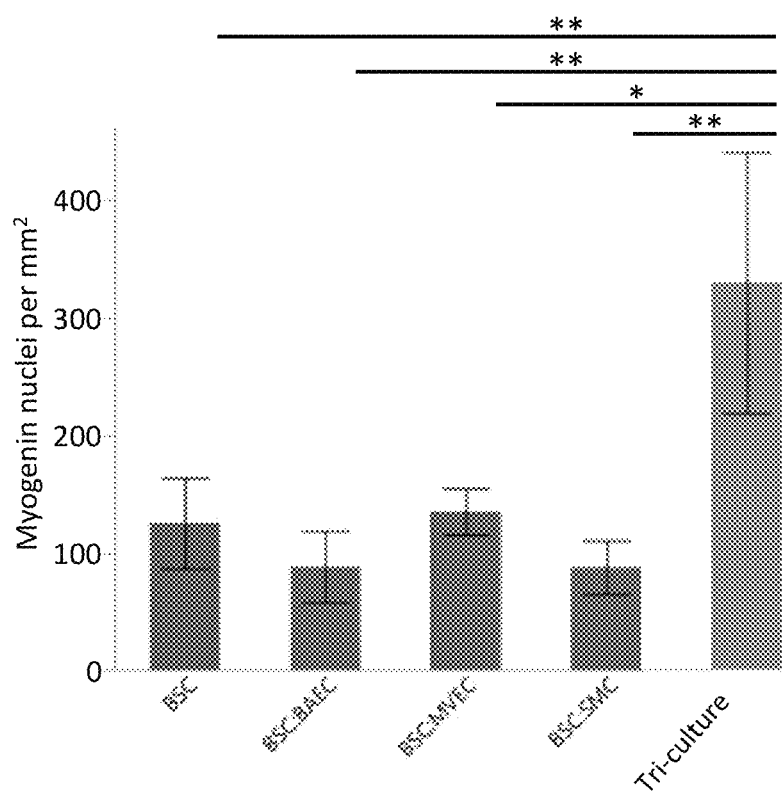
FIGURE 28C

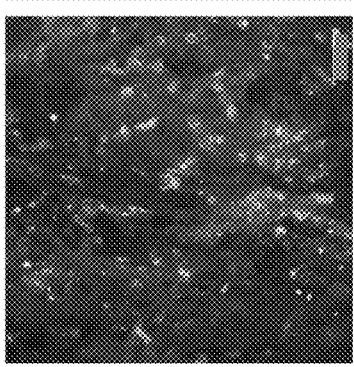
FIGURE 29D
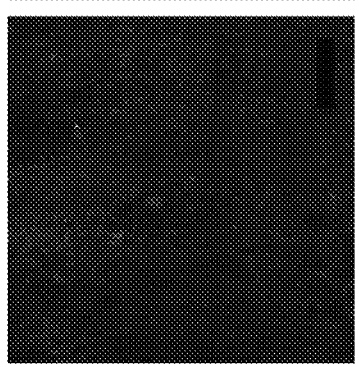
FIGURE 29H
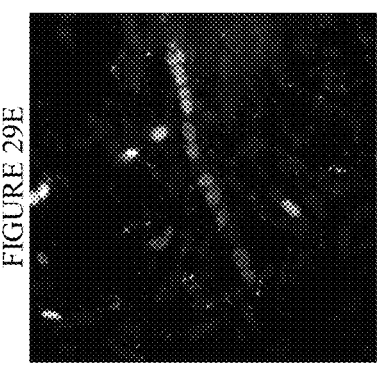
FIGURE 29L
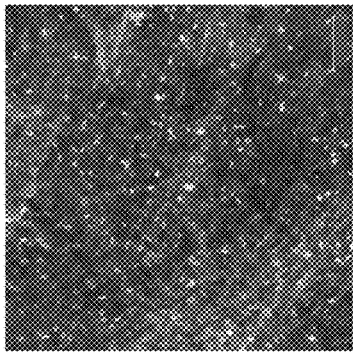
FIGURE 29C
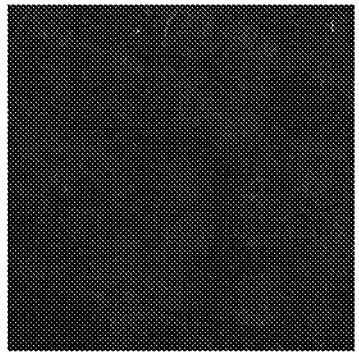
FIGURE 29G
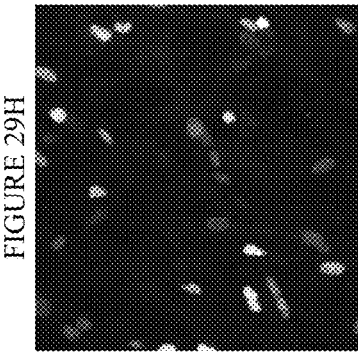
FIGURE 29K
FIGURE 29B
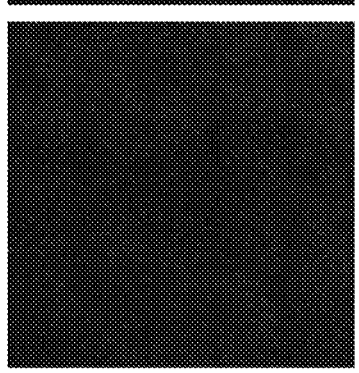
FIGURE 29F
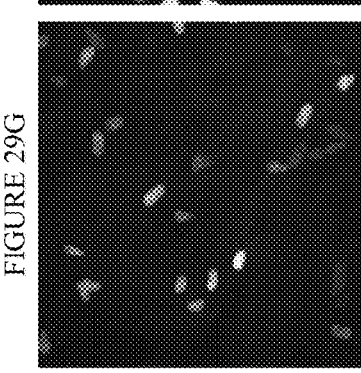
FIGURE 29J
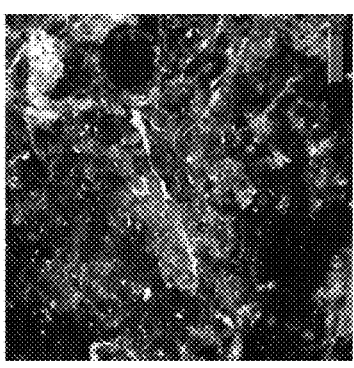
FIGURE 29A
FIGURE 29E
FIGURE 29I

CULTURED MEAT COMPOSITIONS

CROSS REFERENCE

This application is a National Phase of PCT Patent Application No. PCT/IL2018/050776 having International filing date of Jul. 15, 2018, which claims the benefit of priority to U.S. Provisional Patent Application No. 62/532,998 filed Jul. 15, 2017, the contents of which are incorporated herein by reference in their entirety.

FIELD OF INVENTION

The present invention is directed to, inter alia, compositions of cultured meat and methods of producing the same.

BACKGROUND OF THE INVENTION

Cultured meat, also known as engineered or clean meat, is produced from cell culture using tissue engineering techniques and is a prominent alternative for traditional meat production using live animals. In the last decade this notion gained increased attention in public opinion, popular media, investors and the scientific community, notably after the production of the first lab-grown cultured beef burger. Food produced using animals is considered to be inefficient, as the animals consume large amounts of food throughout their lives, which 80-90% of the calories are wasted on the animal's metabolism and the production of non-edible tissues. When comparing different industries, beef has the heaviest environmental impact, however in general, all animal-based products have a larger environmental footprint compared to plant-based products in terms of soil and water demand, and greenhouse gas (GHG) emission. According to the report of the Food and Agriculture Organization of the United Nations, the livestock sector is responsible for 18% of the GHG emissions, uses 30% of earth's terrain or 70% of the arable lands, and 8% of the global freshwater. In addition, the world's demand for meat is expected to double by 2050, meaning traditional meat production systems are not sustainable. Compared to several meat sources, cultured meat is estimated to decrease 7-45% of energy use, 78-96% of the GHG emissions, 99% of land use and 82-96% of water use.

Intensive factory farming and poor animal welfare conditions are a cause for foodborne illnesses such as swine and avian influenza, and the spreading of *E. coli, Salmonella* and *campylobacter* which can be found in meat. Producing meat in a sterile controlled environment could help improve food safety. In addition, 70% of all antibiotics used in the United States are given to farm animals as a food additive which promote the selection of antimicrobial resistant strains and increase the likelihood of multidrug resistant bacteria. Antibiotic overuse is the primary cause for the emergence of antibiotic resistant bacteria, which in the U.S. alone is responsible for an economic burden of $55 b, 2 million infections, 250,000 hospitalizations and at least 23,000 deaths per year. Bacteria with resistance to colistin, the last resort of antibiotics, has recently emerged in Chinese pig farms.

Current cultured meat technology focuses on satellite cell culture. Cells are being grown in two-dimensional (2D) flasks or on micro carriers in suspension, isolated, differentiated and harvested. However, tissues do not consist solely of cells; the extracellular matrix (ECM), which is composed of macromolecules such as glycoproteins and oligosaccharides and gives the tissue its biochemical and biomechanical properties, is a large portion of the tissue. The ECM regulates cells behavior and affects their composition. Thus, ECM producing cells are essential for cultured meat, and processes such as cell harvest must be avoided. Additionally, three-dimensional (3D) cell culture mimics the natural cell environment and is crucial for correct cell behavior which affects cell biochemical content.

SUMMARY OF THE INVENTION

In some embodiments, the present invention is directed to edible compositions comprising myotubes, and method for producing the edible compositions.

The invention is based in part on the findings that a cell culture comprising a plurality of cell types (e.g., satellite cells, ECM-secreting cells and endothelial cells), showed better survival, proliferation and myotube formation, compared to controls, such as when grown on three-dimensional porous scaffold.

The invention is further based in part on the surprising findings that satellite cells, such as non-human satellite cells, had better differentiation activity when co-cultured with low endothelial cells (ECs) concentration rather than with high ECs concentration.

According to one aspect, there is provided a method for producing an edible composition, the method comprising the steps of: (a) incubating a three-dimensional porous scaffold and a plurality of cell types comprising: (i) myoblasts or progenitor cells thereof; and at least one of: (ii) at least one type of extracellular matrix (ECM)-secreting cell; or (iii) endothelial cells or progenitor cells thereof, wherein the myoblasts or progenitor cells thereof and the endothelial cells or progenitor cells thereof are incubated at a ratio ranging between 10:1 to 1:10; and (b) inducing differentiation of myoblasts or progenitor cells thereof into myotubes, thereby producing the edible composition.

In some embodiments, the plurality of cell types comprises myoblasts or progenitor cells thereof, at least one type of extracellular matrix (ECM)-secreting cell, and endothelial cells or progenitor cells thereof.

In some embodiments, the ECM-secreting cell is selected from the group consisting of: stromal cells, fibroblasts, pericytes, smooth muscle cells and progenitor cells thereof.

In some embodiments, the plurality of cell types comprises myoblasts, ECM-secreting cells and endothelial cells.

In some embodiments, the progenitor cell of a myoblast is a satellite cell.

In some embodiments, the endothelial cells are selected from skeletal microvascular endothelial cells, aortic smooth muscle cells, or a combination thereof.

In some embodiments, the plurality of cell types comprises satellite cells, ECM-secreting cells, and endothelial cells.

In some embodiments, the myoblasts or progenitor cells thereof and ECM-secreting cells are incubated at a ratio ranging between 10:1 to 1:1.

In some embodiments, the ECM-secreting cells and endothelial cells are incubated at a ratio ranging between 1:10 to 1:1.

In some embodiments, the satellite cells, the ECM-secreting cells, and the endothelial cells are incubated at a ratio ranging between 10:1:1 to 2:1:10.

In some embodiments, the ECM-secreting cell is a fibroblast, a progenitor cell thereof, or a combination thereof.

In some embodiments, the three-dimensional porous scaffold is selected from the group consisting of: a textured protein, a non-textured protein, and a polysaccharide. In some embodiments, the textured protein is a textured soy protein. In some embodiments, the three dimensional porous scaffold comprises pores with an average diameter ranging from 20 to 1,000 micrometers.

In some embodiments, the plurality of cell types are non-human cells. In some embodiments, the plurality of cells are derived from a livestock mammal.

In some embodiments, the myoblasts or progenitor cells thereof and the three-dimensional porous scaffold are incubated at a ratio ranging from $10^3$ to $10^7$ of the myoblasts or progenitor cells thereof to 10 mg of the three-dimensional porous scaffold. In some embodiments, the three-dimensional porous scaffold further comprises an extracellular matrix.

According to another aspect, there is provided a composition comprising: (a) a three-dimensional porous scaffold; (b) myotubes comprising 100,000-250,000 myotube nuclei per $mm^3$ of the three-dimensional porous scaffold; and (c) a plurality of cell types selected from the group consisting of: (i) myoblasts or progenitor cells thereof; and at least one of: (ii) at least one type of ECM-secreting cells; or (iii) endothelial cells or progenitor cells thereof, wherein the endothelial cells or progenitor cells thereof comprise less than 15% of the plurality of cells.

In some embodiments, the composition is edible.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 9A-9E are micrographs of bovine aorta smooth muscle cells (BAOSMC) (passage 8) seeded in different media. (A) Basal medium; (B) Commercial medium; (C) Fetal bovine serum (15%) supplementation; (D) non-essential amino acids supplementation; and (E) Pyruvate supplementation. Scale bar=100 µm.

FIGS. 10A-10B are vertical bar graphs of the comparison of different media on bovine aorta smooth muscle cells proliferation at passage 9 (A) and passage 10 (B) after 3 days of culturing.

FIGS. 14A-14F are images of fluorescently labeled cell co-cultures comprising BAEC and SMC in different ratios. (A and D) 5:1 BAEC to SMC; (B and E) 1:1 BAEC to SMC. (C and F) are higher magnification of B and E, respectively. A-C are image taken on day 2 and D-F were taken on day 6. BAEC is in red; Scale bar=100 µm.

FIGS. 15A-15E are images of fluorescently labeled cell co-cultures comprising BAEC and BDF in different ratios. (A and C) 5:1 BAEC to SMC; (B and D) 1:1 BAEC to SMC. (E) is a higher magnification of D. A and B are image taken on day 2 and C and D were taken on day 6. BAEC is in red; Scale bar=100 µm.

FIGS. 18A-18G are bright field micrographs of BSC at day 0 of differentiation. (A) Control; (B) bovine fibroblast growth factor (bFGF); (C) epidermal growth factor (EGF); (D) IGF-1 (insulin-like growth factor 1); (E) Pro-LIF (Proliferation media without the growth factor LIF (Leukemia inhibitory factor)); (F) Weaning; and (G) DiI. Scale bar=300 μm.

FIGS. 19A-19G are bright field micrographs of BSC at day 4 of differentiation. (A) Control; (B) bovine fibroblast growth factor (bFGF); (C) epidermal growth factor (EGF); (D) IGF-1 (insulin-like growth factor 1); (E) Pro-LIF; (F) Weaning; and (G) DiI. Scale bar=300 μm.

FIGS. 20A-20H demonstrate myotube formation of BSC at 7 days of differentiation. (A-G) are bright field micrographs of (A) Control; (B) bovine fibroblast growth factor (bFGF); (C) epidermal growth factor (EGF); (D) IGF-1 (insulin-like growth factor 1); (E) Pro-LIF; (F) Weaning; and (G) DiI. Scale bar=300 μm. (H) is a vertical bar graph of % myotube area quantified for each of the different expansion conditions.

FIGS. 23A-23O are immunofluorescent micrographs of tri-cultures grown on PLLA/PLGA scaffolds taken 14 days post seeding. BSC, SMC and BAEC were seeded on PLLA/PLGA scaffolds in different cellular densities of (A-E) 2:1:1 and (F-J) 2:1:5. (K-O) are magnifications of (A-E). Scaffolds were stained for (A, F and K) DAPI; (B, G and L) Myogenin; (C, H and M) DiI; (D, I and N) CD31. (E, J and O) are merged image. Scale bars=100 μm (A-J); 10 μm (K-O).

FIGS. 25A-25H are immunofluorescent micrographs of BSC co-cultured with SMC on textured soy protein scaffolds, 14 days post seeding. Different cellular densities of (A-D) 2:1:1 and (E-H) 2:1:5, were tested. Scaffolds were stained for (A and E) DAPI; (B and F) Myogenin; (C and G) DiI; (D) and (H) are merged images of (A-C) and (E-G), respectively. Scale Bar of =100 μm.

FIGS. 28A-28C are vertical bar graphs showing the effect of the supporting cells on myogenic differentiation and the importance of the different cells' ratio within the culture. Myogenic differentiation is shown for tri-cultures (BSC:SMC:BEC) and controls (co-culture or monoculture) at cellular densities of (A) 2:1:1 and (B) 2:1:5 ON PLLA/PLGA scaffold. (C) 2:1:1 on textured soy protein with a statistical analysis.

DETAILED DESCRIPTION OF THE INVENTION

Figure 1A:
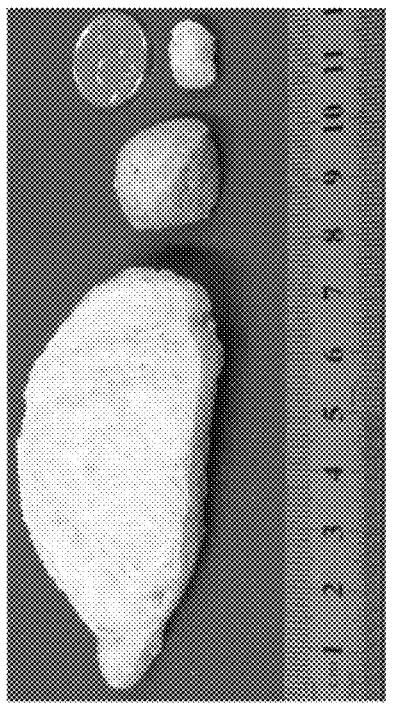
FIGS. 1A-1C are photographs showing commercial TSPs. (A) shows large, medium and small chunks products of TSP. (B) and (C) show 2 other commercial TSP flake products, annotated as TVP (left) and Arcon (right).

The present invention is directed to compositions, kits and methods for producing cultured meat for food consumption. The present invention, in some embodiments, is directed to an edible composition comprising a porous textured protein and a three-dimensional multi-type cellular tissue comprising myoblasts and one or more cell types, attached thereto. The invention is further directed to methods of producing the composition by in-vitro culturing myoblasts and one or more cell types with a three-dimensional porous scaffold (e.g., a porous textured protein) under specific conditions.

In some embodiments, the composition of the invention may be intended for consumption by human beings, non-human animals, or both. In some embodiments, the cultured meat products are food products for human consumption. In other embodiments, the cultured meat products are used for animal feed such as feed for livestock, feed for aquaculture, or feed for domestic pets.

In some embodiments, the invention is directed to a method for producing an edible composition, the method comprising the steps of:
  a. incubating a three-dimensional porous scaffold and a plurality of cell types comprising myoblasts and at least one ECM-secreting cell type selected from the group consisting of: adipocytes, fibroblasts, and progenitor cells thereof; and an endothelial cell or progenitor cell thereof
  b. allowing the plurality of cell types to expand on the three-dimensional porous scaffold; and
  c. inducing myoblasts differentiation into myotubes;
thereby allowing cells to form an edible composition comprising a three-dimensional multi-type cellular tissue comprising muscle cells and the porous textured protein.

As used herein, the term "myotube" refers to a multi-nucleated fiber that is formed from the fusion of a plurality of myoblasts and/or myocytes. As used herein, the term "muscle cell" refers to any cell that contributes to muscle tissue and may encompass: myoblasts, satellite cells (SC), myotubes, myofibers, and myofibril tissues.

In some embodiments, the method includes culturing myoblasts in vitro or ex vivo and allowing these cells to differentiate into specific types of muscle cells such as skeletal muscle cells or smooth muscle cells.

In some embodiments, the invention is directed to an edible composition comprising: a porous textured protein; and a three-dimensional multi-type cellular tissue comprising muscle cells, wherein the three-dimensional multi-type cellular tissue is attached to the porous textured protein, and wherein the three-dimensional multi-type cellular tissue is derived from in-vitro culturing a plurality of cell types comprising: myoblasts and one or more cell types selected from: adipocytes, fibroblasts, smooth muscle cells, endothelial cells and progenitor cells thereof with the porous textured protein.

As exemplified hereinbelow, the composition may comprise fibroblasts which secrete extracellular molecules such as to form the extracellular matrix (ECM) providing further structural and mechanical support to the cells.

As further exemplified hereinbelow, the composition may comprise endothelial cells (EC) or endothelial progenitor cells (EPC) for providing tissue support, providing signaling and/or forming capillary endothelium.

In some embodiments, the three-dimensional multi-type cellular tissue comprises muscle cells including skeletal muscle cells, smooth muscle cells and satellite cells. In some embodiments, the three-dimensional multi-type cellular tissue comprises fat cells (e.g., adipocytes). In some embodiments, the three-dimensional multi-type cellular tissue comprises an extra cellular matrix secreted by specialized cells (e.g., fibroblasts). In some embodiments, the three-dimensional multi-type cellular tissue comprises endothelial cells or capillary endothelium formed by endothelial cells, including, but not limited to aortic endothelial cells and skeletal microvascular endothelial cells. In some embodiments, the three-dimensional multi-type cellular tissue further comprises an extra cellular matrix. In some embodiments, the three-dimensional multi-type cellular tissue further comprises adipocytes. In some embodiments, the three-dimensional multi-type cellular tissue further comprises capillaries.

In some embodiments, the invention is directed to a composition suitable for cell growth comprising a porous textured protein and a cell culture medium. In another embodiment, the composition suitable for cell growth further comprises growth factor, cytokines, bioactive agents, nutrients, amino acids, antibiotic compounds, anti-inflammatory compounds, or any combination thereof. Suitable medium and compounds suitable for viability and growth of the cells are known to one skilled in the art.

In some embodiments, the invention is directed to a composition comprising: a plurality of cell types comprising: myoblasts and one or more cell types selected from: adipocytes, fibroblasts endothelial cells, smooth muscle cells, and progenitor cells thereof, attached to a porous textured protein.

In some embodiments, the invention provides a kit comprising: a three-dimensional porous scaffold (e.g., a porous textured protein); and a plurality of cell types comprising: myoblasts and one or more cell types selected from: adipocytes, fibroblasts, smooth muscle cells, endothelial cells, and progenitor cells thereof. In some embodiments, the kit is for producing an edible composition. In some embodiments, the kit further comprises at least one component selected from: a cell culture medium, growth factor, differentiation medium, differentiation inducers. In some embodiments, the kit further comprises a cell culture medium. In another embodiment, the cell culture medium is selected from a dry powder media, a granulated preparation, an aqueous liquid or a media concentrate. In some embodiments, the plurality of cell types are frozen. In some embodiments, the kit further comprises instructions for use.

Plurality of Cell Types

As will be appreciated by one skilled in the art, numerous cell types or population of cells may be cultured with the three-dimensional porous scaffold, so as to form a three-dimensional multi-type cellular tissue architecture. In some embodiments, the one or more cell types are selected from: myoblasts, ECM-secreting cells, endothelial cells.

In some embodiments, the one or more cell types is a progenitor cell of a myoblast. In some embodiments, the one or more cell types is a progenitor cell of an ECM-secreting cell. In some embodiments, the one or more cell types is a progenitor cell of an endothelial cell.

As used herein, a progenitor cell comprises a mesenchymal stem cell (MSc), an embryonic stem cell (ESc), an adult stem cell, a differentiated ESc, a differentiated adult Stem cell, and an induced pluripotent Stem cell (iPSc). As used herein, the term "progenitor cell" refers to a cell capable of giving rise to differentiated cells in multiple lineages, such as, myoblasts, fibroblasts, adipocytes, stromal cells, fibroblasts, pericytes, smooth muscle cells, and endothelial cells. "Progenitor cells" differ from stem cells in that they typically do not have the extensive self-renewal capacity.

In some embodiments, a cell of the plurality of cell types of the present invention is a progenitor cell. In some embodiment, the progenitor cell is cultured in a monoculture. In some embodiment, the progenitor cell is differentiated in a monoculture. In some embodiment, the progenitor cell is differentiated in a monoculture and is then incubated on a three-dimensional porous scaffold with a plurality of cells according to the method of the present invention. A non-limiting example include, but is not limited to, culturing and differentiating a mesenchymal stem cell into a myoblast cell and thereafter seeding and subsequently incubating differentiated myoblast on a three-dimensional porous scaffold. Methods of culturing and inducing differentiation of progenitor cells to mature cells would be apparent to one of ordinary skill in the art.

In some embodiments, the plurality of cell types comprises myoblasts and fibroblasts. In some embodiments, the plurality of cell types comprises myoblasts, fibroblasts and/or fibroblasts progenitor cells. In some embodiments, the plurality of cell types comprises myoblasts, fibroblasts and adipocytes. In some embodiments, the plurality of cell types comprises myoblasts, fibroblasts, adipocytes, and/or fibroblast progenitor cells and/or adipocyte progenitor cells. In some embodiments, the plurality of cell types comprises myoblasts, fibroblasts and endothelial cells. In some embodiments, the plurality of cell types comprises myoblasts, fibroblasts and endothelial cells, and/or fibroblast progenitor cells, and/or endothelial progenitor cells. In some embodiments, the plurality of cell types comprises myoblasts and smooth muscle cells. In some embodiments, the plurality of cell types comprises myoblasts, smooth muscle cells and endothelial cells. In some embodiments, the plurality of cell types comprises myoblasts, smooth muscle cells, endothelial cells, and adipocytes. In some embodiments, the plurality of cell types comprises myoblasts, fibroblasts, endothelial cells, and adipocytes. In some embodiments, the plurality of cell types comprises myoblasts, fibroblasts, endothelial cells, adipocytes and/or fibroblast progenitor cells, and/or adipocyte progenitor cells, and/or endothelial progenitor cells.

In some embodiments, the plurality of cell types are obtained from a live animal and cultured as a primary cell line. For a non-limiting example, the cells may be obtained by biopsy and cultured ex vivo. For another non-limiting example, the cells may be obtained from commercial sources.

In some embodiments, the plurality of cell types are derived from stem cells such as pluripotent embryonic stem cells. In another embodiment, mesenchymal stem cells (MSCs) are used. As known to one skilled in the art, MSCs may give rise to muscle cells, fat cells, bone cells, and cartilage cells. In another embodiment, the cells are induced pluripotent stem cells (iPS or iPSCs). In another embodiment, the cells are derived from totipotent embryonic stem cells such as cells from the blastocyst stage, fertilized eggs, placenta, or umbilical cords of these animals.

In some embodiments, the plurality of cell types are derived from non-human cells. In some embodiments, the plurality of cell types are derived from non-human cells selected from the group consisting of: mammals, birds, fishes, invertebrates, reptiles, amphibians, and combinations thereof. In some embodiments, the plurality of cell types are derived from mammals. In some embodiments, the plurality of cell types are derived from non-human mammals. In some embodiments, the plurality of cell types are derived from livestock mammals. As used herein, "livestock" comprises any domestic mammal, semi-domestic mammal or captive wild mammal. Non-limiting examples of non-human mammals include: antelope, bear, beaver, bison, boar, camel, caribou, cattle, deer, elephant, elk, fox, giraffe, goat, hare, horse, ibex, kangaroo, lion, llama, moose, peccary, pig, rabbit, seal, sheep, squirrel, tiger, whale, yak, and zebra, or combinations thereof. In some embodiments, the plurality of cell types are derived from bird cells. Non-limiting examples of birds include: chicken, duck, emu, goose, grouse, ostrich, pheasant, pigeon, quail, and turkey, or combinations thereof. In some embodiments, the plurality of cell types are derived from fishes. Non-limiting examples of fishes include: bass, catfish, carp, cod, eel, flounder, fugu, grouper, haddock, halibut, herring, mackerel, mahi, marlin, orange roughy, perch, pike, pollock, salmon, sardine, shark, snapper, sole, swordfish, tilapia, trout, tuna, and walleye, or combinations thereof. In some embodiments, the plurality of cell types are derived from invertebrates. Non-limiting examples of invertebrates include: lobster, crab, shrimp, clams, oysters, mussels, and sea urchin. In some embodiments, the plurality of cell types are derived from reptiles. Non-limiting examples of reptiles include: snake, alligator, and turtle. In some embodiments, the plurality of cell types are derived from amphibians. Non-limiting example of amphibians includes frogs.

Seeding and Culturing Cells

As will be appreciated by one skilled in the art, each type of cell used in the composition and method described herein may have a preferred or optimal range of cell density and prefers medium or growth factors suitable for the cell's viability. In some embodiments, each cell type is seeded in a specific cell density. In some embodiments, cells are seeded simultaneously or in a sequential manner.

In some embodiments, myoblasts are seeded in a cell density of $10^3$ to $10^7$ cells to 10 mg of the porous textured protein. In some embodiments, different cell types are seeded in a specific ratio. In some embodiments, a ratio of seeded myoblast to seeded fibroblasts ranges between 1:1,000 and 1,000:1. In some embodiments, a ratio of seeded myoblast and seeded fibroblasts to seeded endothelial cells ranges between 1:20 and 20:1. In some embodiments, a ratio of seeded myoblast and seeded fibroblasts to seeded adipocytes ranges between 1:5000 and 5000:1. In some embodiments, a ratio of seeded satellite cells to seeded smooth muscle cells ranges between 5:1 and 1:5. In some embodiments, a ratio of seeded satellite cells to seeded skeletal microvascular endothelial cells ranges between 10:1 to 1:10. In some embodiments, a ratio of seeded smooth muscle cells to seeded skeletal microvascular endothelial cells ranges between 10:1 to 1:10. In some embodiments, a ratio of seeded satellite cells to seeded smooth muscle cells to seeded skeletal microvascular endothelial cells ranges between 10:1:1 to 2:1:10. In one embodiment, a ratio of seeded satellite cells to seeded smooth muscle cells to seeded skeletal microvascular endothelial cells ranges between is 2:1:1 to 2:1:5, or any ratio there between. In one embodiment, a ratio of seeded satellite cells to seeded smooth muscle cells to seeded skeletal microvascular endothelial cells ranges between is 2:1:1 to 2:1:2, or any ratio there between. In one embodiment, a ratio of seeded satellite cells to seeded smooth muscle cells to seeded skeletal microvascular endothelial cells ranges between is 2:1:1 to 2:1:3, or any ratio there between. In one embodiment, a ratio of seeded satellite cells to seeded smooth muscle cells to seeded skeletal microvascular endothelial cells ranges between is 2:1:1 to 2:1:4, or any ratio there between. Each possibility represents a separate embodiment of the present invention.

In some embodiments, the seeded cell density and incubated cell density are comparably the same.

In one embodiment, "coverage %" refers to the area or volume of a porous scaffold that is in contact with cells or myotubes. In another embodiment, coverage % refers to the area or volume of a porous scaffold that is occupied by cells or myotubes. As used herein, cells in contact with the scaffold are on, within, or a combination thereof.

In some embodiments, coverage % of the plurality of cells is at least 10%, at least 20%, at least 30%, at least 40%, at least 50%, at least 60%, at least 70%, at least 80%, at least 90, or at least 99%. In some embodiments, coverage % of the plurality of cells is 5-20%, 15-30%, 25-40%, 35-50%, 45-60%, 55-70%, 65-80%, 75-90%, 85-100%, or any range therebetween. Each possibility represents a separate embodiment of the present invention.

In some embodiments, the coverage % of satellite cells are at least 35%, at least 50%, at least 60%, at least 70%, at least 80%, at least 90, or at least 99%. In some embodiments, coverage % of satellite cells 25-40%, 35-50%, 45-60%, 55-70%, 65-80%, 75-90%, 85-100%, or any range therebetween. Each possibility represents a separate embodiment of the present invention.

In some embodiments, the coverage % of endothelial cells is 2% at most, 5% at most, is 10% at most, is 15% at most, is 20% at most, is 25% at most, is 30% at most, is 35% at most, is 40% at most, is 45% at most, or is 50% at most. In some embodiments, the coverage % of endothelial cells is 5-15%, 10-25%, 20-35%, 30-50%, or any range therebetween. Each possibility represents a separate embodiment of the present invention.

In some embodiments, endothelial cells are used to increase proliferation of myoblasts or progenitor cells thereof. In some embodiments, the endothelial cells inhibit differentiation of myoblasts or progenitor cells thereof to myotubes. In some embodiments, endothelial cells support growth and proliferation of myoblasts or progenitor cells thereof. In some embodiments, endothelial cells are not required for differentiation of myoblasts or progenitor cells thereof. In some embodiments, according to the method of the present invention, endothelial cells activity (e.g., secretion of myogenic agents, supporting myoblasts growth, survival, or both) is maintained for a defined period. In some embodiments, the defined period for endothelial activity is the period required for myoblasts or progenitor cells thereof to achieve a coverage of at least 30%, at least 40%, at least 50%, at least 60%, at least 70%, at least 80%, at least 90%, or at least 99% of the three-dimensional porous scaffold. In some embodiments, the defined period for endothelial activity is the period required for myoblasts or progenitor cells thereof to achieve a coverage of at least 30%, In some embodiments, the coverage % of myotubes is at least 5%, at least 20%, at least 35%, at least 50%, at least 70%, at least 85%, at least 90%, at least 90%, or at least 99%. In some embodiments, the coverage % of myotubes is 1-10%, 5-20%, 15-35%, 30-50%, 40-65%, 60-85%, 80-90%, 90-100%, or any range therebetween. Each possibility represents a separate embodiment of the present invention.

In some embodiments, myotubes of the composition of the present invention comprise 10,000-100,000 nuclei per mm$^3$ of the three-dimensional porous scaffold, 10,000-100,000 nuclei per mm$^3$ of the three-dimensional porous scaffold 15,000-200,000 nuclei per mm$^3$ of the three-dimensional porous scaffold 50,000-500,000 nuclei per mm$^3$ of the three-dimensional porous scaffold 5,000-1,000,000 nuclei per mm$^3$ of the three-dimensional porous scaffold 100,000-250,000 nuclei per mm$^3$ of the three-dimensional porous scaffold 10,000-1,500,000 nuclei per mm$^3$ of the three-dimensional porous scaffold, or any range therebetween. Each possibility represents a separate embodiment of the present invention.

As would be apparent to a skilled artisan, ECM affects myoblasts differentiation to myotubes. In some embodiments, ECM-secreting cells utilized according to methods of the present invention improve myoblasts differentiation. In some embodiments, ECM-secreting cells improved myoblasts differentiation by simulating tissue physical properties.

As defined herein, the terms "improved" and "increased" are interchangeable.

In some embodiments, improved is by at least 5%, by at least 20%, by at least 35%, by at least 50%, by at least 75%, by at least 90%, by at least 100%, by at least 250%, by at least 500%, by at least 750%, by at least 1,000%, by at least 2,500%, or by at least 5,000%. In some embodiments, improved is by 5-15%, 10-35%, 25-45%, 40-70%, 65-90%, 85-150%, 100-500%, or 250-1,000%. Each possibility represents a separate embodiment of the present invention.

Non-limiting examples of a tissue physical properties include, but are not limited to stiffness, porosity, flexibility, rigidity, etc.). A tissue can be physically defined according to its Young's modulus, viscosity modulus, or other parameters, all of which would be apparent to one of ordinary skill in the art.

In some embodiment, the method of the present invention further comprises a step of sterilizing the porous textured protein. In some embodiments, the porous textured protein is sterilized prior to seeding or incubating the plurality of cell types. In some embodiments, sterilization is by gamma radiation. In another embodiment, sterilization is ethanol-based sterilization. Procedures of sterilization would be apparent to a person of ordinary skill in the art.

A skilled artisan will appreciate that the seeding and/or the culturing of cells is performed in the presence of a cell culture medium. In another embodiment, the cell culture medium comprises growth factor, cytokines, bioactive agents, nutrients, amino acids, antibiotic compounds, anti-inflammatory compounds, or any combination thereof. Suitable medium and compounds suitable for viability and growth of the cells are known to one skilled in the art.

Growth factors that can be used in the methods and compositions of the invention include but are not limited to platelet-derived growth factors (PDGF), insulin-like growth factor (IGF-1). PDGF and IGF-1 are known to stimulate mitogenic, chemotactic and proliferate (differentiate) cellular responses. The growth factor can be, but is not limited to, one or more of the following: PDGF, e.g., PDGF AA, PDGF BB; IGF, e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-P1, TGF β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor.

As exemplified hereinbelow, in the case of bovine-derived cells, an optimized satellite cells (SC) expansion media (i.e., Pro-LIF media) comprises Bovine SC (BSC) growth media (99%), amphotericin B (AB/AM; 1% 1×), $ZnCl_2$ (50 µM), EGF (62 ng/ml), IGF-1 (100 ng/ml), and bFGF (10 ng/ml).

As exemplified hereinbelow, in the case of bovine-derived cells, an optimized SC growth media comprises DMEM/HEPES (43.5%), Ham's F-10 Nutrient Mix (43.5%), Fetal bovine serum (10%), MEM NEAA (1% 1×), GlutaMAX (1%), and AB/AM (1% 1×).

As exemplified hereinbelow, in the case of bovine-derived cells, an optimized SC differentiation media comprises DMEM/HEPES (97%), Donor Horse Serum (2%), AB/AM (1% 1×), IGF-1 (100 ng/ml), and EGF (62 ng/ml).

Porous Scaffold

In some embodiments, plurality of cells of the invention are incubated with a porous scaffold. As used herein, the term "scaffold" refers to a structure comprising a material that provides a surface suitable for adherence/attachment, maturation, differentiation, and proliferation of cells. A scaffold may further provide mechanical stability and support. A scaffold may be in a particular shape or form so as to influence or delimit a three-dimensional shape or form assumed by a population of proliferating cells. In some embodiments, a porous scaffold of the invention is three dimensional.

In some embodiments, an average pore diameter of the porous scaffold ranges from 20 micrometers (µm) to 1000 µm, 20 µm to 900 µm, 20 µm to 800 µm, 20 µm to 700 µm, 20 µm to 600 µm, 20 µm to 500 µm, 20 µm to 400 µm, 20 µm to 300 µm, 20 µm to 200 µm, 20 µm to 100 µm, 50 µm to 1000 µm, 50 µm to 900 µm, 50 µm to 800 µm, 50 µm to 700 µm, 50 µm to 600 µm, 50 µm to 500 µm, 50 µm to 400 µm, 50 µm to 300 µm, 50 µm to 200 µm, 50 µm to 100 µm, 100 µm to 1000 µm, 100 µm to 900 µm, 100 µm to 800 µm, 100 µm to 700 µm, 100 µm to 600 µm, 100 µm to 500 µm, 100 µm to 400 µm, 100 µm to 300 µm, 100 µm to 200 µm, 500 µm to 1000 µm, 500 µm to 900 µm, 500 µm to 800 µm, 500 μm to 700 μm, or 500 μm to 600 μm. Each possibility represents a separate embodiment of the present invention. In some embodiments, an average pore diameter of the porous scaffold ranges from 20 μm to 1000 μm.

In some embodiments, the porous scaffold is edible. In some embodiments, the porous scaffold comprises a textured protein. In some embodiment, the porous scaffold comprises a polysaccharide. In some embodiments, the textured protein is a textured vegetable protein. In some embodiments, the textured protein is a textured soy protein (e.g., TSP).

The term "texture" is used herein to refer to a rigid mass, or flexible mass, of individual cells which can be readily formed into various sizes, shapes and configurations and which is non-dispersible in water.

Suitable particulate textured protein materials for use herein can consist of from 30% to 100% protein, on a dry weight basis, and from 0% to 70% materials associated with the protein source material or added adjuvant materials. Examples of adjuvant materials are carbohydrates, vitamins, flavors, colorings or others. In some embodiments, the protein particles consist of 50% to 100% protein, or 50% to 80% protein by dry weight.

Suitable un-textured proteins which can be texturized to form textured particulate protein materials are available from a variety of sources. For a non-limiting example, a source of such proteins is a vegetable protein and certain fungal proteins; however, animal protein can be employed. Examples of suitable animal proteins are casein, collagen, and egg white. Examples of suitable vegetable protein sources are soybeans, safflower seed, corn, peanuts, wheat, wheat gluten, peas, sunflower seed, chickpea, cottonseed, coconut, rapeseed, sesame seed, leaf proteins, gluten, single cell proteins such as yeast, and the like.

Another example of a suitable protein source is mushroom. In some embodiment, a mushroom protein source comprises a protein amount of 15-20% (w/w), 20-30% (w/w), 28-45% (w/w), or 10-40% (w/w) by dry weight.

Generally, if the protein source is a vegetable protein, the protein prior to use is placed in a relatively pure form. Thus, for example if the protein source is soybeans, the soybeans can be solvent extracted, such as with hexane, to remove the oil therefrom. The resulting oil-free soybean meal contains about 50% protein.

The soybean meal can be processed in a known manner to remove carbohydrates and obtain products with higher levels of protein, for example, soy protein concentrates containing about 70% protein or soy protein isolates containing about 90% or more protein. In turn, a variety of suitable prior art processes can be employed to convert the soybean meal, concentrate, isolate and other edible protein bearing materials into suitable texturized particulate protein materials.

Suitable methods for converting un-textured animal and vegetable protein bearing materials into particulate textured proteins are disclosed, for example, in the following U.S. Pat. No. 2,682,466, granted Jun. 29, 1954, to Boyer; U.S. Pat. No. 3,142,571, granted Jul. 28, 1964, to Kitchel; U.S. Pat. No. 3,488,770, granted Jan. 6, 1970, to Atkinson; U.S. Pat. No. 3,498,794, granted Mar. 3, 1970, to Calvert et al; U.S. Pat. No. 3,759,715, granted Sep. 18, 1973, to Loepiktie et al.; U.S. Pat. No. 3,778,522, granted Dec. 11, 1973, to Strommer; U.S. Pat. No. 3,794,731, granted Feb. 26, 1974, to Dannert et al.; U.S. Pat. No. 3,814,823, granted Jun. 4, 1974, to Yang et al.; and commonly assigned U.S. patent application Ser. No. 248,581, filed Apr. 28, 1972, now U.S. Pat. No. 3,840,679, granted Oct. 8, 1974 to Liepa et al.; all these patents being incorporated herein by reference.

In alternative embodiments, the porous textured protein may be substituted by other porous compositions which are ingestible edible as well as chewable. As used herein the terms "ingestible" and "edible" refer to compositions which can be safely taken into the body. These compositions include those which are adsorbed, and those which are not absorbed as well as those which are digestible and non-digestible. As used herein, the term "chewable" refers to a composition which can be broken/crushed into smaller pieces by chewing prior to swallowing. One skilled in the art will appreciate that a suitable edible composition may be selected according to physical properties (e.g., Young's modulus, viscosity modulus, stiffness, etc.) to a desired use (e.g., consumption by a human adult).

According to the method of the present invention, a plurality of cell types is seeded on a three dimensional porous scaffold per se. In some embodiments, a plurality of cell types seeded on a three dimensional porous scaffold requires no solidifying agents. In some embodiments, a plurality of cell types seeded on a three dimensional porous scaffold requires solidifying agents. In some embodiments, solidifying agents increase the adherence or attachment of the plurality of cell types to a three dimensional porous scaffold. Non-limiting examples for solidifying agents include but are not limited to thrombin or fibrin.

As used herein, the terms "gelation agent" and "solidifying agent" are interchangeable.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); "Bacteriophage Methods and Protocols", Volume 1: Isolation, Characterization, and Interactions, all of which are incorporated by reference. Other general references are provided throughout this document.

Materials and Methods

Textured Soy Protein

Figure 1B:
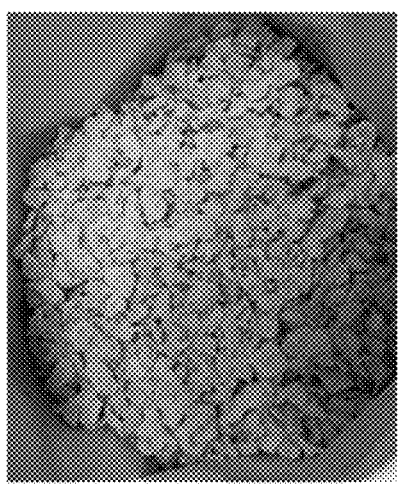
Figure 1C:
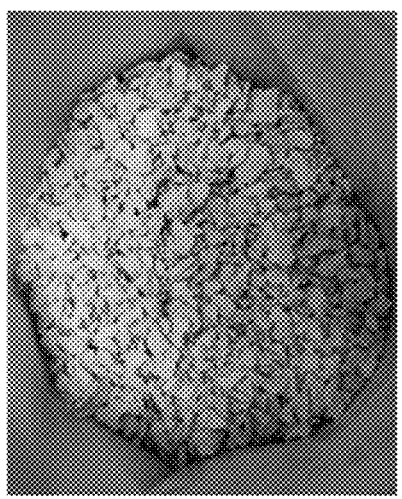

Textured soy protein (TSP) is commercially available as several different products. TSP scaffolds were prepared out of 5 different sources of commercial TSP—3 TSP chunks (FIG. 1A) bought at a local health food store and 2 TSP flakes (FIGS. 1B-1C) bought from ADM. TSP was sterilized in gamma radiation of 25-40 kGy for 3.5 hours and kept in sterile environment or using 70% (v/v) ethanol for 15 minutes. Followed by 3 washes with PBS.

TSP Scaffold Preparation

Figure 2B:
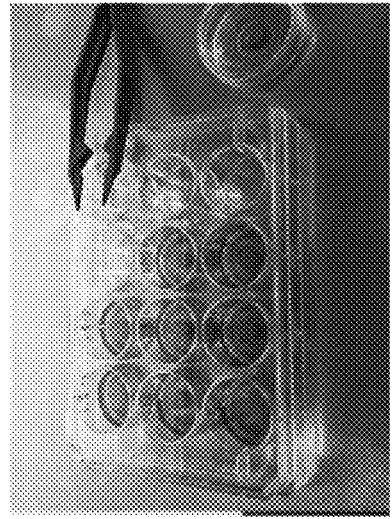
FIGS. 2A-2B are photographs showing TSP scaffold preparation (A), and cell containing TSP scaffolds (B).
Figure 2A:
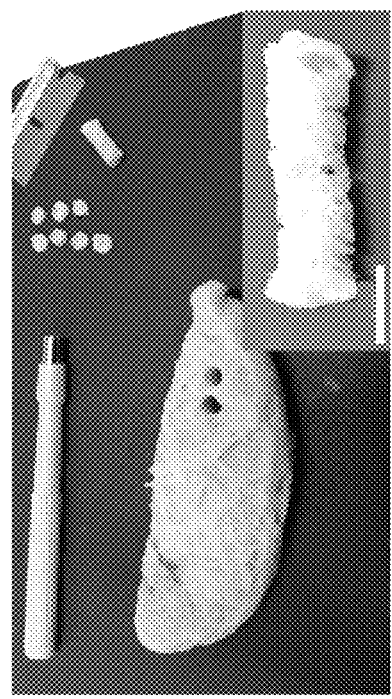

TSP flakes (Arcon or TVP) were chosen using Graefe Forceps so as to have similar thickness of about 200-400 µm (per 1 layer). Flakes were incubated in 5-10 ml of sterile DDW at 37° C. overnight (in a 50 ml falcon). The next day the flakes were cut into 6 mm scaffolds using 6 mm biopsy punch inside the hood on a non-TC 10 cm plate. Using a Pasteur pipette the scaffold was remove from the biopsy punch and transferred into a falcon with 5 ml growth media. TSP chunks were incubated in DDW at 37° C. overnight. Then chunks were cut into cylinders (inset of FIG. 2A) using a biopsy punch and cut into 1 mm thick disks using a knife (FIG. 2A). The scaffolds were then placed in 5 ml growth media.

Scaffold Seeding

Per a single scaffold, $2 \times 10^6$ BSC were transferred to an Eppendorf and centrifuged for 4 minutes at 1,500 rcf. Meanwhile each scaffold was put in a well of a Non-TC 6-well plate with 50 µl with growth media. After centrifugation the media was aspirated from the Eppendorf tube leaving a pellet of cells. Then, per each Eppendorf the following steps were performed: (1) the media was thoroughly aspirated from the scaffold using forceps to gently squeeze the scaffold and media residues were vacuumed; (2) 7 µl of thrombin (20 MHU/ml sigma in PBS) and 7 µl of fibrinogen (15 mg/ml sigma in PBS) were added; (3) the cells were then seeded on the scaffold; (4) scaffolds were incubated at 37° C. for 30 min till drying and then were added with 2 ml of expansion media into the well; (5) the day after, scaffold was transferred to a new container (e.g., 24 non-TC well with coverslip bottom) using sterile Graefe forceps into and was added with 2 ml of expansion media; (6) the scaffold was incubated at 37° C. and 5% $CO_2$; (7) the scaffold maintained in the expansion media for 7 days; (8) media was replaced every 2 days (2 ml); (9) after 7 days the expansion media was replaced by BSC differentiation media; and (10) differentiation media was replaced every 2 days for a period of 5 days.

Cell Culture

Bovine satellite cells (BSC) were cultured in BSC proliferation media 43.5% DMEM/HEPES (Gibco), 43.5% F-10 Nut Mix (Gibco), 10% FBS (HyClone), 1% NEAA (Gibco), 1% GlutaMAX (Gibco) and 1% Penicillin-Streptomycin-Amphotericin B Solution (Biological Industries (Ab/Am, BI) supplemented with 50 µM $ZnCl_2$ (Millipore), 62 ng/ml EGF (R&D Systems), 100 ng/ml IGF-1 (R&D Systems), 10 ng/ml LIF (R&D Systems) and 10 ng/ml bFGF (R&D Systems). BSC differentiation medium was comprised of DMEM/HEPES supplemented with 2% FBS and 1% Ab/Am. Red Fluorescent Protein (RFP) expressing Dermal Fibroblasts (Lonza, USA) are cultured in Dulbecco's minimal essential medium (DMEM; Gibco Life Technologies) supplemented with 10% FBS (HyClone; Thermo Fisher Scientific), 1% nonessential amino acids (Biological Industries), 0.2% β-mercaptoethanol (Biological Industries), and 100 units/ml penicillin and 0.1 mg/ml streptomycin (Pen-Strep Solution, Biological Industries, Israel). Myoblasts (American Type Culture Collection) are cultured in DMEM, supplemented with 10% FBS, 2.5% HEPES buffer (Biological Industries) and 1% Pen-strep solution. Myoblast differentiation medium is comprised of DMEM supplemented with 2% FBS, 2.5% HEPES buffer and 1% Pen-strep solution. All incubations are performed in a 5% (v/v) $CO_2$ humidified atmosphere at 37° C. Bovine smooth muscle cell (SMC; CellAplications) were cultured as described in table 3. Bovine aortic endothelial cells (BAEC; CellAplications) were cultured in the commercial media (CellAplications).

Bovine skeletal muscle microvascular ECs (BSkMVEC; AngioProteomie) were cultured in ECM commercial medium (ScienCell) with 10% total FBS. Bovine dermal fibroblasts (BDF; Sciencell) were cultured either in the commercial medium (FM-2; ScienCell) or in DMEM high glucose medium supplemented with 15% FBS.

Immunohistochemistry

Scaffolds are rinsed twice in PBS, then fixed in 4% paraformaldehyde (PFA) for 20 minutes on a shaker. The scaffolds are washed thrice with PBS for 5 minutes on a shaker, and then permeabilized with 0.3% Triton X-100 (Bio Lab Ltd) for 10 min. Next, the scaffolds are washed thrice with PBS for 5 minutes and then immersed in 5% Bovine Serum Albumin (BSA; Millipore) in PBS overnight at 4° C. The scaffolds are incubated with 250 μl Primary antibody (in 5% BSA in PBS) for 3 hours at room temperature. Following incubation, the scaffolds are washed 4 times with PBS for 5 minutes. Then, the cells are incubated in room temperature for 3 hours with Secondary antibody (in PBS) and 4',6-diamidino-2-phenylindole (DAPI, 1:1000 in PBS; Vector Laboratories) in a plate covered with tin foil on shaker. The scaffolds are washed with PBS for 5 minutes on a shaker and imaged with a confocal microscope (LSM 700, Zeiss).

Bovine Aortic Smooth Muscle Cells (BAMSC)

The effect on cell proliferation of four different media formulations were compared with a commercial medium (BSM) (Table 3). At the beginning of the experiment, cells were at passage 8 and were seeded at 4,000 cells/cm$^2$ in a 6-well plate. At day 3, cells were trypsinized, counted with a hemocytometer, and reseeded at 4,000 cells/cm$^2$. The experiment was performed twice, using the same cells for each condition. One-way ANOVA was used to test statistical significance.

Cell Growth Kinetics

Approximately $4\times10^3$ cells/cm$^2$ were seeded and counted every day with a hemocytometer, over a period of six days. Counted values were plotted.

Cell Staining

Supporting cells (BDF or BASMC) were stained with 3 ml fresh media with 15 μl of lipophilic-tracers DiD (1 mg/ml diluted in absolute ethanol; # D7757, Molecular Probes®, USA). Bovine endothelial cells (BECs; BAEC or BSkMVEC) were stained with 3 ml fresh media with 5 μl of lipophilic-tracers DiI (3 mg/ml diluted in absolute ethanol; # D, Molecular Probes®, USA) and incubated for 30 min in 37° C. Following one wash with medium and then two more washes with PBS, the cells were trypsinized and ready for seeding as described hereinbelow.

Seeding Cells on a Porous Scaffold

Bovine ECs ($1.25\times10^5$) and supporting cells ($0.25\times10^5$) were resuspended in 5 μl of a 1:1 mixture of 1 5 mg/ml fibrinogen (Sigma Aldrich) and 20 NIHu/ml thrombin (Sigma Aldrich). The fibrinogen solution was prepared by diluting lyophilized human fibrinogen (Sigma Chemical) in 40 mM glycine-tris buffer. The thrombin solution was prepared by diluting thrombin (Sigma Aldrich) in 40 mM calcium chloride. The co-culture suspension was then seeded onto 4 mm diameter round PLLA-PLGA porous scaffolds and allowed to solidify in 12-well non-tissue plates for 30 min, in an incubator (37° C., 5% $CO_2$). After solidification, 2 ml of endothelial culture media (ECM, ScienCell) supplemented with additional 5% FBS and 2 nM VEGF was added to each well. Medium was replaced every other day.

For further tuning of the ratio of cells seeded on porous scaffolds, the cells were seeded as described above with the following modifications: the cells were first seeded with 1:1 medium (bEBM, AngioProteomie: commercial medium of the supporting cells) and the cells were resuspended in 5 μl of a 1:1 mixture of 15 mg/ml fibrinogen (Johnson and Johnson) and 2 U/ml thrombin (Johnson and Johnson).

Bovine Satellite Cells (BSC) Differentiation in 2D $5\times10^4$ BSC (Passage 4) were seeded on a TC 24-well plate with coverslip bottom in triplicates. Cells were grown according to a myotube formation protocol, as follows: 4 days in growth media and 7 days in differentiation media (t=0 refers to the point when using differentiation media started). The cells were then stained for Hoechst and Myogenin at days −1 and 7.

Optimization of BSC Differentiation in 2D

BSC (Passage 4) were grown for 4 days in expansion media with different GFs (as described below) and were then grown for 7 days in differentiation media (DMEM-HEPES+ 2% HS). Day 0 was defined as the day the media was replaced to differentiation media.

The expansion media formulations included: (1) Control—Growth media (No GF added); (2) bovine fibroblast growth factor (bFGF; 10 ng/ml); (3) Epidermal growth factor (EGF; 62 ng/ml); (3) Insulin-like growth factor 1 (IGF-1; 100 ng/ml); (4) Pro-LIF; bFGF 10 ng/ml, EGF 62 ng/ml, IGF-1 100 ng/ml, and $ZnCl_2$ 50 μM); (6) GF weaning: Pro-LIF media for 3 days, then 3 washes with growth media (every 5 minutes), then 1 day growth media; (7) cells were stained with DiI grown in growth media—to check whether DiI, a fluorescent color added for tracking the cells, affects cell differentiation.

The inventors further checked the effect of GFs: IGF-1, EGF and their combination during the differentiation phase. BSC (Passage 4) were grown for 4 days in growth media and were then grown for 7 days in differentiation media with different GFs (as described below). The differentiation media formulations included: (1) Control—the original differentiation media (DMEM-HEPES+2% HS); (2) IGF-1 (100 ng/ml); (3) EGF (62 ng/ml); and (4) IGF-1 (100 ng/ml)+EGF (62 ng/ml). Cells were visualized using brightfield microscopy for all cases described above.

Optimization of BSC Expansion on 3D Scaffolds

For this purpose, a double factorial experiment (seeding volume and expansion media formulation) was set with duplicates, as follows: (1) Seeding volume and cell number: (a) 10 μl seeding volume and $1\times10^6$ BSC; (b) 10 μl seeding volume and $2\times10^6$ BSC; and (c) 20 μl seeding volume and $2\times10^6$ BSC. (2) Expansion media: (a) Growth media; and (b) Pro-LIF media (growth media+bFGF+EGF+IGF-1+$ZnCl_2$). BSC (Passage 4) were stained using DiI and were then seeded on porous scaffolds (Arcon) according to the Arcon seeding protocol.

Optimization of BSC Differentiation on 3D Scaffolds

For this purpose, a double factorial experiment (expansion media in the first week and differentiation media in the second week) was set, as follows: (1) Expansion media: (a) Control (Growth media); (b) Pro-LIF; and (c) Pro-LIF–bFGF. (2) Differentiation media either alone or supplemented as follows: (a) Control (differentiation media with 2% Horse serum); (b)+IGF-1; (c)+EGF; and (d)+IGF-1+ EGF. BSC (Passage 4) were stained using DiI. Four (4) mm porous scaffolds were seeded with $0.5\times10^6$ BSC (Passage 4) in 5 μl of fibrin. The cells were imaged at days 2, 7 and 14 post seeding. The scaffolds were then stained for desmin. Staining was done according a whole mount staining protocol with the primary polyclonal antibody 1:100 goat a desmin (Santa Cruz Cat. No. sc-7559) and the secondary antibody Alexa 1:200 488 Donkey a goat (Invitrogen Cat. No. A11055).

Staining Bovine Satellite Cells (BSC) Prior Seeding

BSC were stained with 1 ml fresh media with 5 μl of lipophilic-tracers DiI (3 mg/ml diluted in absolute ethanol, Molecular Probes®, USA) and incubated for 30 min in 37° C. Following 1 wash with medium and then 2 washes with PBS, after which the cells were trypsinized and ready for seeding as described.

Seeding Cells on PLLA-PLGA

Bovine satellite cells (BSC) with or without bovine ECs (BEC) and with or without supporting cells were resuspended in 6 μl of a 1:1 mixture of 15 mg/ml fibrinogen (Sigma Aldrich) and 20 NIHU/ml thrombin (Sigma Aldrich). The fibrinogen solution was prepared by diluting lyophilized human fibrinogen (Sigma Chemical) in 40 mM glycine-tris buffer. The thrombin solution was prepared by diluting thrombin (Sigma Aldrich) in 40 mM calcium chloride. The cells' suspension was then seeded onto 4 mm diameter round PLLA-PLGA scaffolds and allowed to solidify in 12-well non-tissue plates for 30 min, inside an incubator (37° C., 5% $CO_2$). After solidification, 1 ml of 1:1 mixture of endothelial culture media with BSC growth medium (Pro-LIF) was added to each well. Medium was replaced every other day. After a week, the medium was changed to BSC differentiation medium (supplemented with IGF-1 and EGF) for additional week.

Seeding Cells on Textured Soy Protein Scaffolds

Bovine satellite cells (BSC) with or without bovine ECs and with or without supporting cells were resuspended in 15 μl of a 1:1 mixture of 15 mg/ml fibrinogen (Sigma Aldrich) and 20 NIHU/ml thrombin (Sigma Aldrich). The fibrinogen solution was prepared by diluting lyophilized human fibrinogen (Sigma Chemical) in 40 mM glycine-tris buffer. The thrombin solution was prepared by diluting thrombin (Sigma Aldrich) in 40 mM calcium chloride. The cells' suspension was then seeded on both sides of 6 mm diameter round textured soy protein scaffolds and allowed to solidify in 12-well non-tissue plates for 45 min, inside an incubator (37° C., 5% $CO_2$). After solidification, 1 ml of 1:1 mixture of endothelial culture media with BSC growth medium (Pro-LIF) was added to each well. Medium was replaced every other day. After a week, the medium was changed to BSC differentiation medium (supplemented with IGF-1 and EGF) for additional week.

Two seeding ratios and 2 types of endothelial cells (and their appropriate medium) were tested as described in the tables below:

TABLE 1

Seeding on PLLA\PLGA scaffolds

| Culture | BSC | SMC | BEC | TOTAL |
|---|---|---|---|---|
| Tri-culture 2:1:1 | 250,000 | 125,000 | 125,000 | 500,000 |
| Tri-culture 2:1:5 | 125,000 | 62,500 | 312,500 | 500,000 |
| Co-culture 2:1 | 250,000 | 125,000 | | 375,000 |
| Co-culture 2:1 | 250,000 | | 125,000 | 375,000 |
| Monoculture control for 2:1:1 | 250,000 | | | 250,000 |
| Co-culture 2:1 | 125,000 | 62,500 | | 187,500 |
| Co-culture 2:5 | 125,000 | | 312,500 | 437,500 |
| Monoculture control for 2:1:5 | 125,000 | | | 125,000 |

TABLE 2

Seeding on textured soy protein scaffolds

| Culture | BSC | SMC | BEC | TOTAL |
|---|---|---|---|---|
| Tri-culture 2:1:1 | 750,000 | 375,000 | 375,000 | 1,500,000 |
| Tri-culture 2:1:5 | 375,000 | 187,500 | 937,500 | 1,500,000 |
| Monoculture control for 2:1:1 | 750,000 | | | 750,000 |
| Co-culture 2:1 | 750,000 | 375,000 | | 1,125,00 |
| Co-culture 2:1 | 750,000 | | 375,000 | 1,125,00 |
| Monoculture control for 2:1:5 | 375,000 | | | 375,000 |
| Co-culture 2:1 | 375,000 | 187,500 | | 562,500 |
| Co-culture 2:5 | 375,000 | | 937,500 | 1,312,500 |

Seeding Cells on Gelfoam

Bovine satellite cells (BSC) were resuspended in 15 μl of BSC growth media. The cells' suspension was then seeded on both sides of 6 mm diameter celinder Gelfoam© scaffolds and allowed to solidify in 12-well non-tissue plates for 30 min, inside an incubator (37° C., 5% $CO_2$). After solidification, 1 ml of BSC growth medium (Pro-LIF) was added to each well. Medium was replaced every other day. After a week, the medium was changed to BSC differentiation medium (supplemented with IGF-1 and EGF) for additional week.

Cell Growth on Scaffolds

One and two weeks post seeding, DiI labeled-BSC seeded on PLLA/PLGA and Arcon scaffolds were imaged using confocal microscopy for assessing cell growth.

Whole-Mount Immunofluorescence Staining

Two weeks post seeding, scaffolds were fixed with 4% paraformaldehyde (PFA; Electron Microscopy Sciences) for 20 min, followed by three washes with PBS (Gibco® Life Technologies). Permeabilization was achieved by incubating the scaffolds for 15 min at room temperature (RT), in 0.3% Triton X-100 (Bio Lab Ltd). After three washes with PBS, scaffolds were incubated overnight in blocking buffer (10% FBS, 1% (w/v) glycine and 0.01% triton, in PBS), at 4° C. Scaffolds were then incubated overnight at 4° C. with primary antibodies: 1:50 goat-anti-CD31 (Santa Cruz), with or without 1:50 mouse anti-MYH (Santa Cruz), diluted in blocking buffer. Following several washes with PBS, samples were incubated with 1:400 donkey anti-goat Alexa Fluor®488 (Jackson ImmunoResearch), 1:50 Alexa Flour 647-conjugated mouse anti-myogenin (Santa Cruz) and 1:1, 000 DAPI (4',6-diamidino-2-phenylindole, Sigma-Aldrich) with or without 1:300 Alexa Flour 647 anti-mouse, for 3 h at RT. Following several washes with PBS, scaffolds were immediately imaged with a Zeiss LSM700 confocal microscope (Carl Zeiss), using the Zen software. Image processing and further analyses were performed using FIJI software. PLLA/PLGA scaffolds were also whole-mount immunofluorescence-stained one week post seeding.

Cryosectioning and Trichrome Staining

At the end of each experiment, scaffolds were incubated overnight in a 30% (w/v) sucrose solution at 4° C. Scaffolds were then embedded in optimal cutting temperature (OCT) compound (Tissue-Tec, USA), and frozen for subsequent cryosectioning. The OCT embedded scaffolds were cryosectioned into 5 and 10 μm-thick sections. 5 μm-thick sections were then stained according to trichrome standard staining protocol.

Example 1

Three Dimensional Structure Analysis of a TSP Porous Scaffold

Figure 3A:
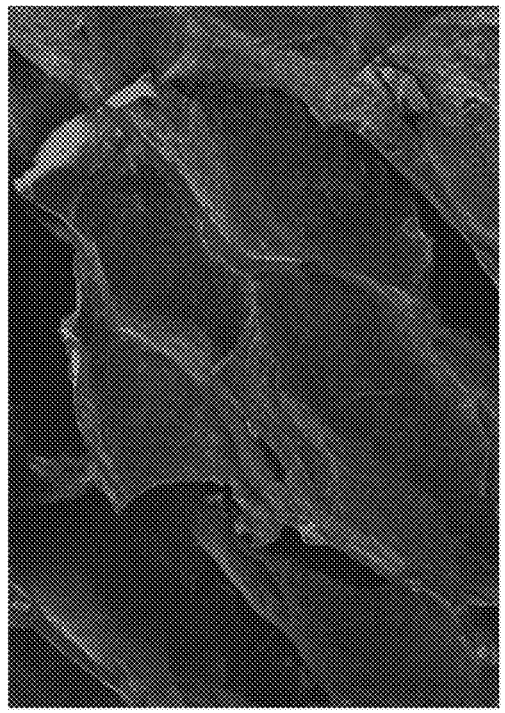
FIGS. 3A-3B are 100× magnification SEM images of big TSP (A) and medium TSP (B).
Figure 4A:
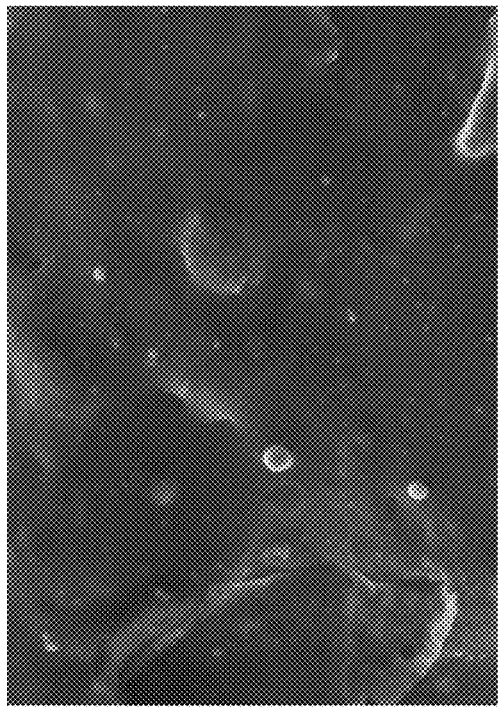
FIGS. 4A-4B are $2\times10^5$ magnification SEM images of big TSP (A) and medium TSP (B).
Figure 3B:
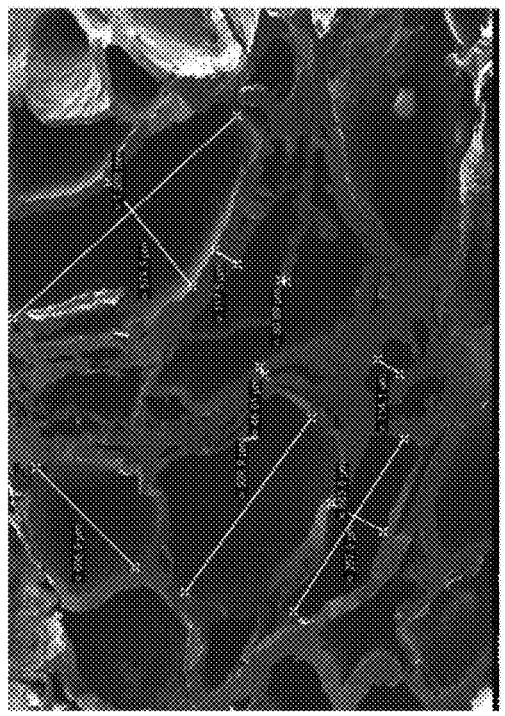
Figure 4B:
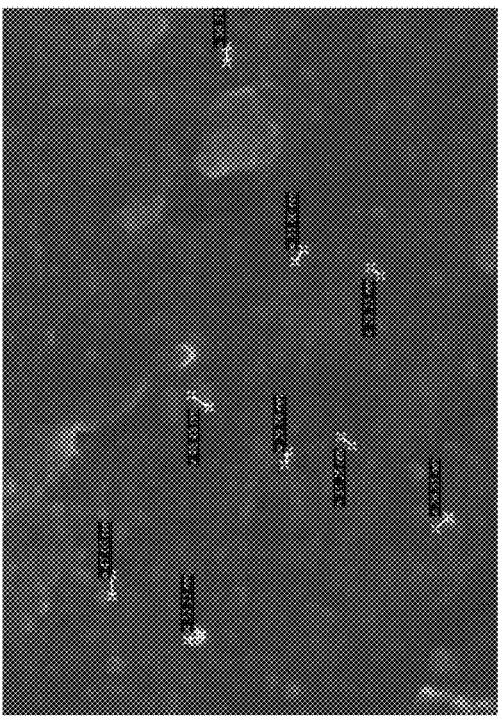

TSP scaffolds were examined using scanning electron microscopy (SEM) to analyze their three-dimensional (3D) structure both at the micron and the nano scale. The 100× images showed the TSP was porous with 100-1,000 µm pore size, which can be used for cell culture. It was shown that the wall in the big-TSP were thicker compared to the medium sourced TSP (FIGS. 3A and 3B). SEM images ($2 \times 10^5$ magnification) of the large TSP showed that the TSP comprised 30 nm ball shaped protein clusters. Analysis of the medium TSP showed more amorphous glue-like material between those clusters (FIGS. 4A and 4B).

Example 2

Growth and Proliferation of Fibroblasts Cultured on a Porous Scaffold

Figure 5C:
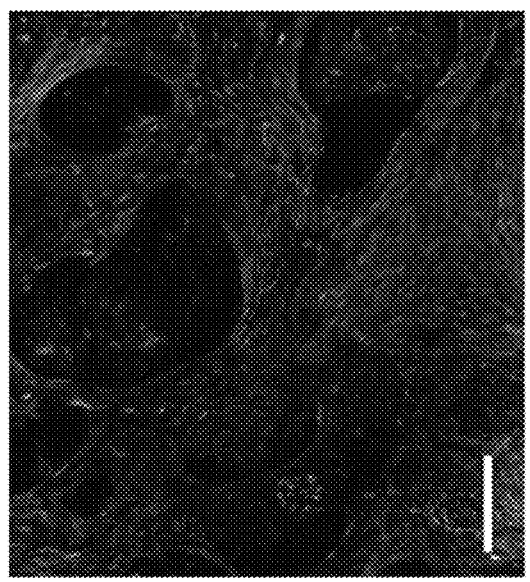
FIGS. 5A-5C are confocal microscopy images of TSP scaffolds populated with fibroblasts and endothelial cells on days 8 (A), 18 (B), and 21 (C) following seeding of fibroblasts.
Figure 5B:
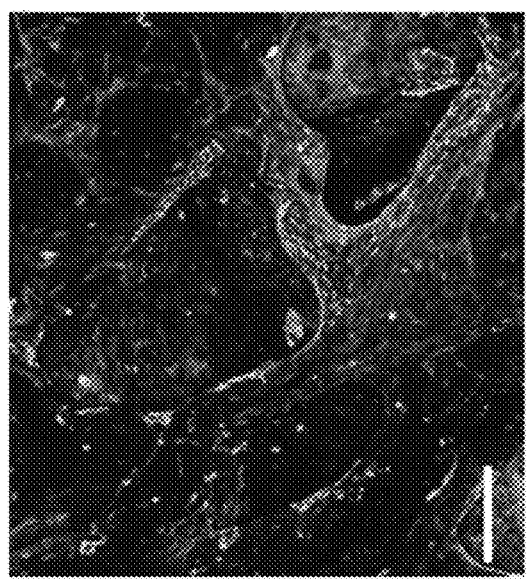
Figure 5A:
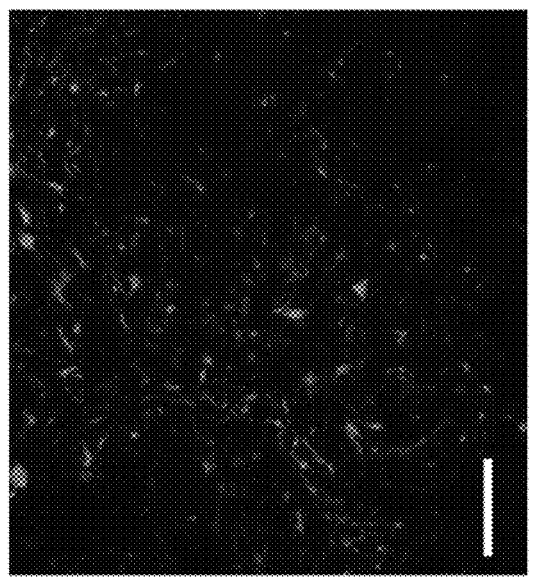
Figure 6:
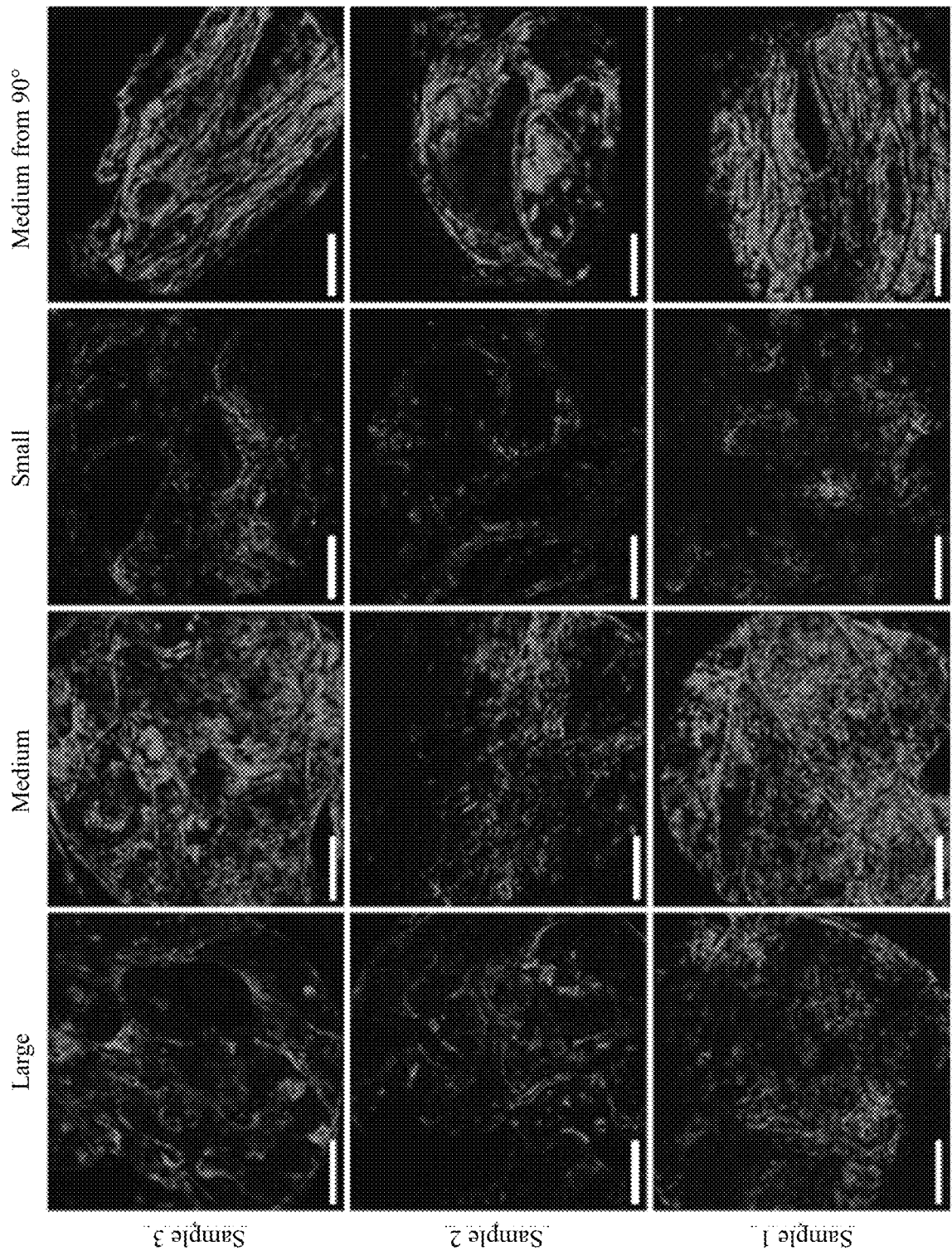
FIG. 6 is confocal microscopy images taken 14 days following seeding of 200,000 fibroblast (red) onto three different samples of scaffolds (samples 1-3) obtained from different sources denoted as Large, Medium, Small, and Medium from 90°, scaffolds denoted as Medium from 90° were cut from the pore side of the TSP in the scaffold preparation procedure TSP scaffolds. Scale bar=1 mm.

Attachment and proliferation of fibroblasts on a TSP scaffold were examined. First, 50,000 dermal fibroblasts which were labeled with RFP, were seeded on a TSP scaffold, and cultured. Following 14 days of incubation, the TSP scaffold, which was populated with dermal fibroblasts, was additionally seeded with 200,000 endothelial cells, and incubated for additional 7 days. Samples of TSP populated with cells were immune-stained and imaged using a confocal microscopy, at 8, 18 and 21 days following seeding of the fibroblasts. Results demonstrated that the fibroblasts proliferated and covered the TSP scaffold even when seeded at the low cell number of 50,000 cells (FIG. 5A). Following the seeding of the endothelial cells (FIG. 5B), the endothelial cells gathered into clusters (FIG. 5C). Next, scaffolds from each scaffold source and scaffolds cut from 90° to the surface direction of the TSP were examined. Each of the scaffolds was seeded with 200,000 fibroblast cells and incubated for 14 days. Results demonstrated that the fibroblasts cells grew and proliferated on the big and medium TSP scaffold (FIG. 6). These results indicate that cells can fill the scaffold after 14 days of culture.

Example 3

Growth of Myoblasts Cultured on a Porous Scaffold

In order to assess the applicability of generating a muscle tissue, experiments were conducted to examine whether muscle cells can grow on the TSP scaffold.

Figure 7:
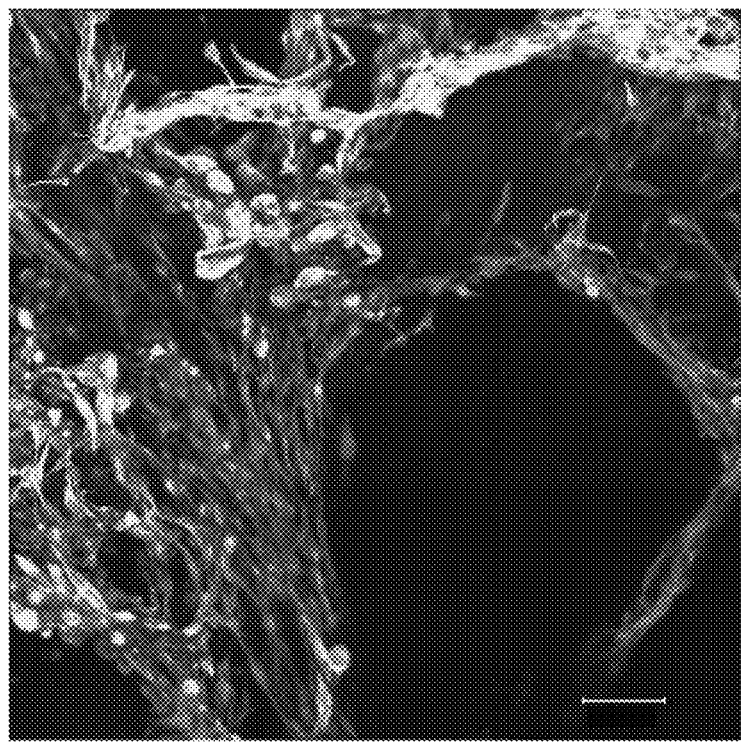
FIG. 7 is a confocal microscopy image of myoblast cultured on a TSP scaffold for 14 days (DAPI, Desmin).

For this purpose, $0.5 \times 10^6$ myoblasts were seeded on TSP scaffolds and cultured in the presence of a differentiation medium which was low on serum and thus fitted better for cultured meat production. The images of the myoblasts at day 14 (FIG. 7) showed that the myoblasts proliferated on the TSP scaffold, indicating that cells can fill the scaffold after 14 days of culture.

Example 4

Proliferation of Bovine Skeletal Muscle Cells Cultured on TSP

Figure 8:
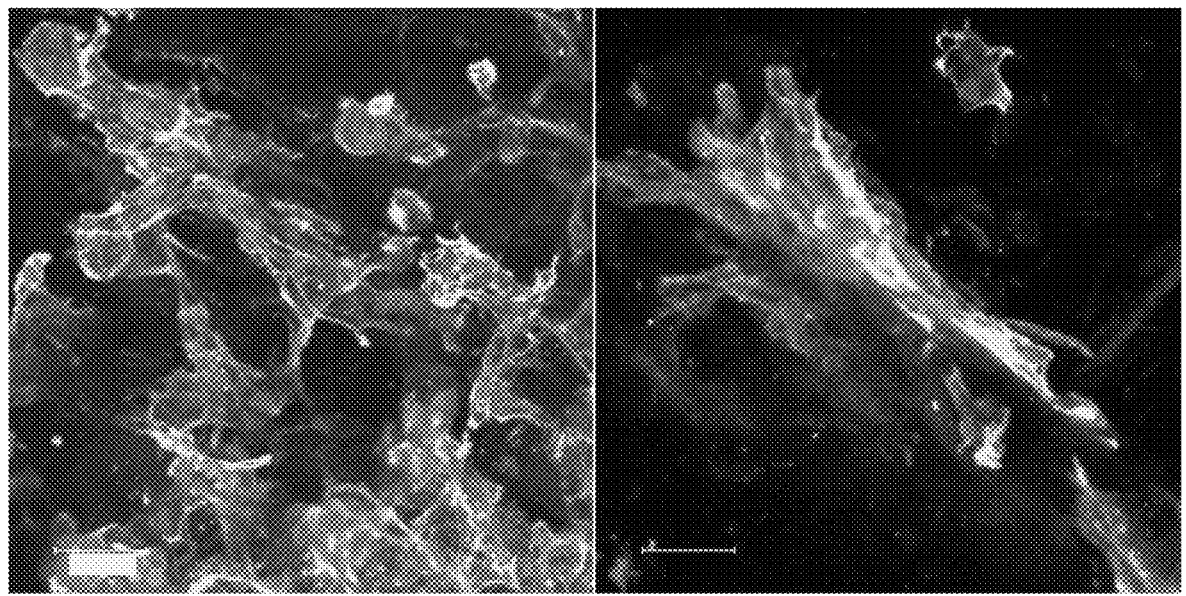
FIG. 8 is confocal microscopy images of bovine skeletal muscle cells cultured on a TSP scaffold for 14 days (DAPI, Phalloidin).

In order to assess the applicability for human consumption, bovine skeletal muscle cells (bSkMC) were seeded on the TSP scaffold. Specifically, $0.5 \times 10^6$ bSkMC cells were seeded on each scaffold and cultured in the presence of a differentiation medium. On day 14, cells were imaged using a confocal microscopy. The images (FIG. 8) showed that the bSkMC proliferated on the TSP scaffold, indicating that the TSP is applicable for cultured meat production.

Example 5

Proliferation of Bovine Aortic Smooth Muscle Cells (SMC)

The inventors examined the effect of four different media formulations compared to a commercial medium (BSM; table 3) on the proliferation of SMC seeded (FIGS. 9A-9E) in media described hereinbelow.

TABLE 3

| Formulations of different media tested on SMC | | | | | |
|---|---|---|---|---|---|
| | 1 | 2 (basal) | 3 | 4 | 5 |
| BSM | + | − | − | − | − |
| Dulbecco's Modified Eagle Medium (DMEM) | − | + | + | + | + |
| Fetal bovine serum (FBS) | − | 10% | 15% | 10% | 10% |
| Penicillin-Streptomycin (PS) | − | 1% | 1% | 1% | 1% |
| Non-essential amino acids (NEAA) | − | − | − | 1% | − |
| Sodium pyruvate | − | − | − | − | 1 mM |

At day 3, no significant difference in cell number could be detected across the five different media (FIG. 10A). On day 3 of a following experiment (FIG. 10B), a significant difference between the four different treatments was observed (P<0.01) and a post-hoc analysis revealed that the number of cells exposed to pyruvate-supplemented medium was significantly higher compared to NEAA supplemented medium and 15% FBS supplemented medium (with P-values<0.05 and <0.01, respectively). The difference between the commercial medium and the sodium pyruvate-supplemented medium was marginally significant (P=0.052). Therefore, the inventors proceeded with sodium pyruvate supplemented medium (1 mM) for BAOSMC culturing.

Example 6

Growth Characterization of BDF and SMC Under Defined Conditions

Figures 11A, 11B:
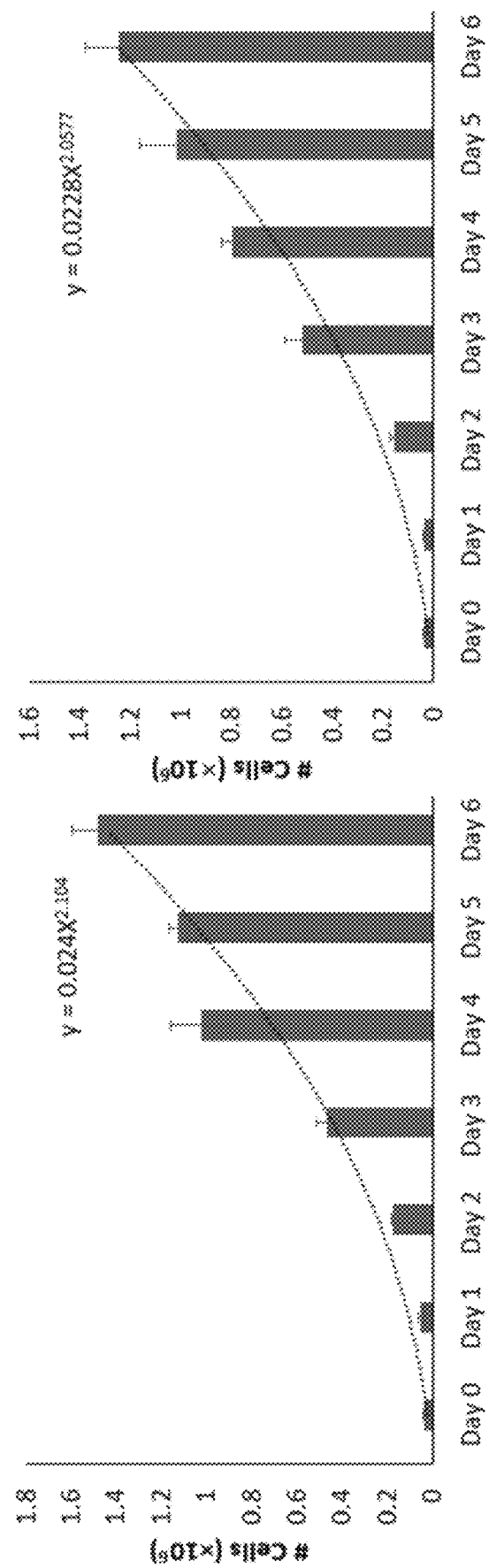
FIGS. 11A-11B are graph demonstrating growth kinetics of Bovine dermal fibroblasts (BDF) (A) and Bovine aorta smooth muscle cells (BAOSMC; B).
Figure 12A:
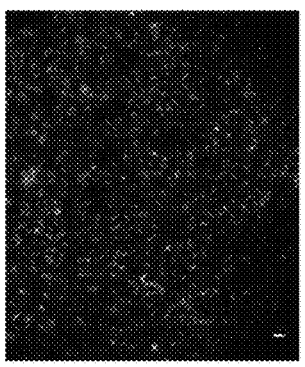
FIGS. 12A-12L are images of fluorescently labeled bovine aortic endothelial cells (BAEC) cells seeded in co-culture with supporting cells on day 2 (A, D, G and J), 6 (B, E, H and K), and 8 (C, F, I and L). BAEC cells were seeded with either bovine aortic smooth muscle cells (SMC; A-F) or bovine dermal fibroblasts (BDF; G-L). A-C and G-I are tile scans of 3×3 in ×5 magnification. D-F and J-L are ×20 magnifications. Scale bar=100 µm.
Figure 12B:
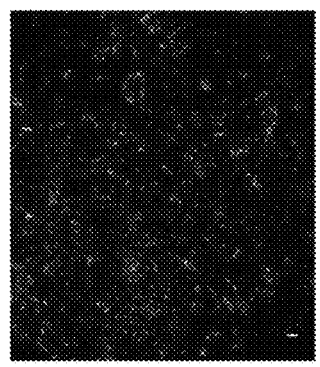
Figure 12C:
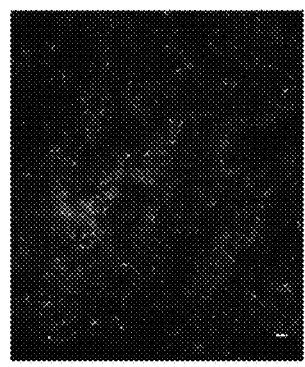
Figure 12D:
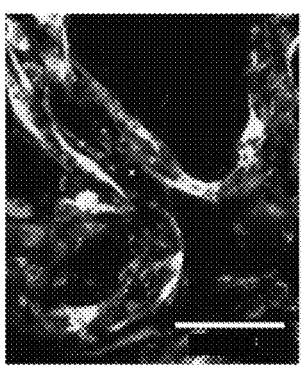
Figure 12E:
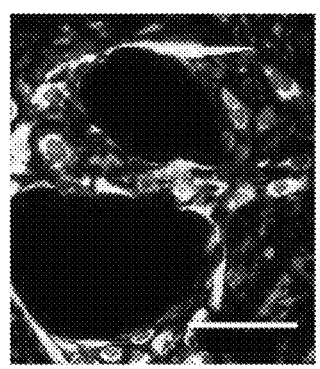
Figure 12F:
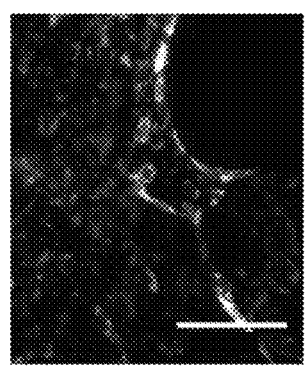
Figure 12G:
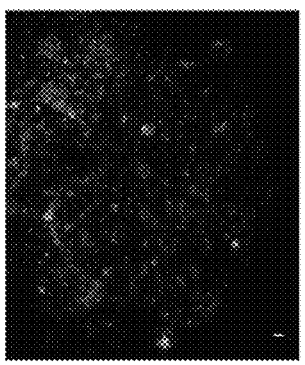
Figure 12H:
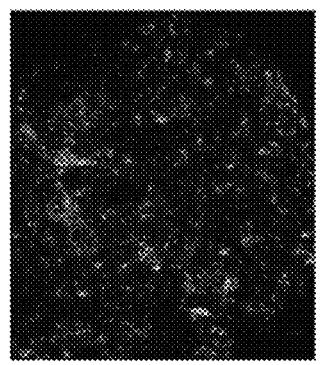
Figure 12I:
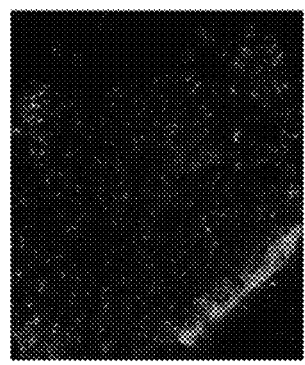
Figure 12J:
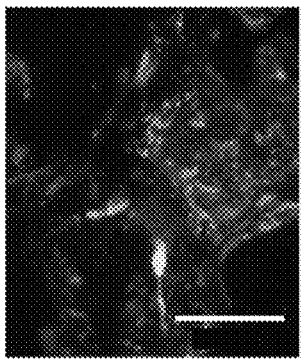
Figure 12K:
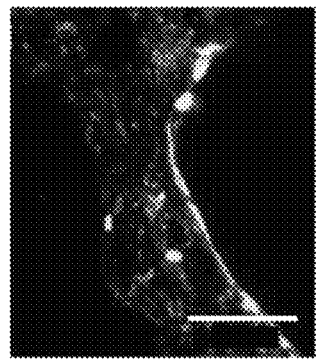
Figure 12L:
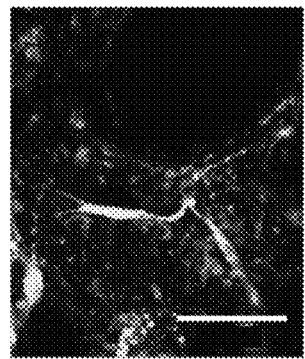

After having defined custom media formulations, the inventors have examined their growth kinetics under these conditions (Example 5). The growth rates of BDF (FIG. 11A) and BAOSMC were found to be highly similar (FIG. 11B).

Example 7

Effect of EC and Supporting Cells on Vascularization

Figure 13A:
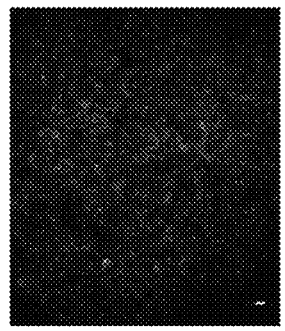
FIGS. 13A-13L are images of fluorescently labeled bovine skeletal muscle microvascular endothelial cells (BSKMVEC) cells seeded in co-culture with supporting cells on day 2 (A, D, G and J), 6 (B, E, H and K), and 8 (C, F, I and L). BSKMVEC cells were seeded with either bovine aortic smooth muscle cells (SMC; A-F) or bovine dermal fibroblasts (BDF; G-L). A-C and G-I are tile scans of 3×3 in ×5 magnification. D-F and J-L are ×20 magnifications. Scale bar=100 µm.
Figure 13B:
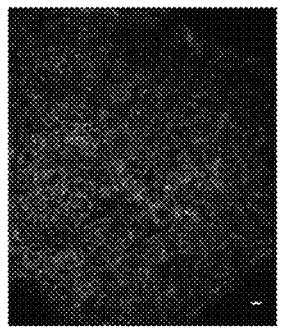
Figure 13C:
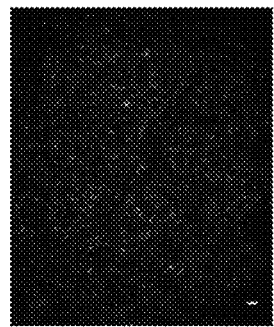
Figure 13D:
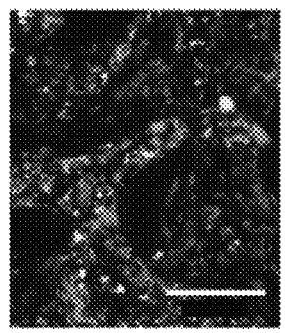
Figure 13E:
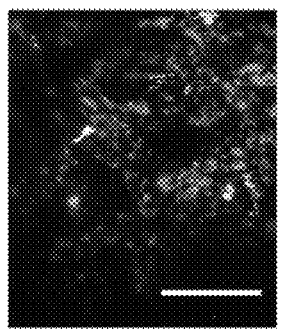
Figure 13F:
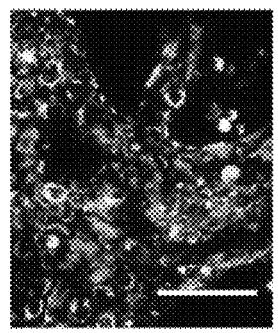
Figure 13G:
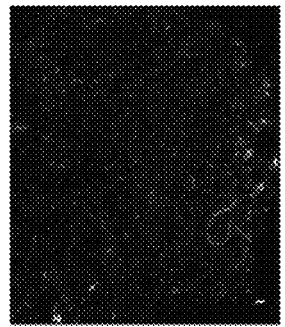
Figure 13H:
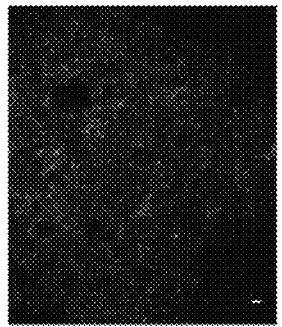
Figure 13I:
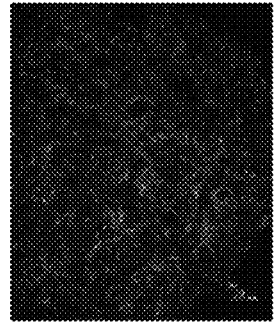
Figure 13J:
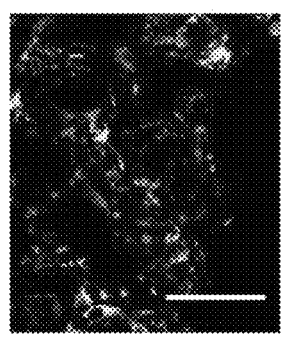
Figure 13K:
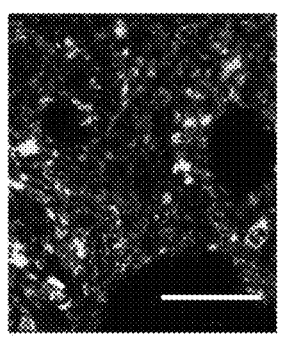
Figure 13L:
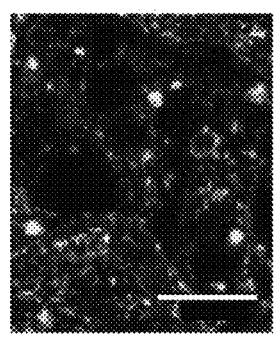
Figure 16A:
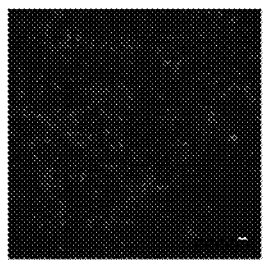
FIGS. 16A-16L are images of fluorescently labeled cell co-cultures comprising BAEC and SMC in different ratios. (A-D) 1:3 BAEC to SMC; (E-H) 1:1 BAEC to SMC; and (I-L and F) 5:1 BAEC to SMC. (B, D, F, H, J, and L) are higher magnification of (A, C, E, G, I, and K), respectively. (A, B, E, F, I and J) are image taken on day 2 and (C, D, G, H, K and L) were taken on day 6. BAEC is in red; Scale bar=100 µm.
Figure 16B:
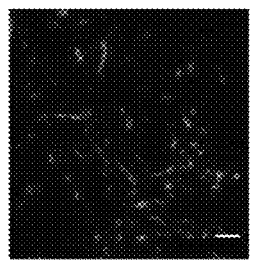
Figure 16C:
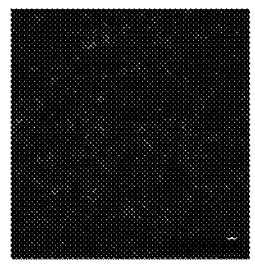
Figure 16D:
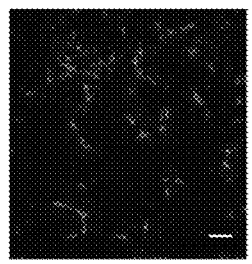
Figure 16E:
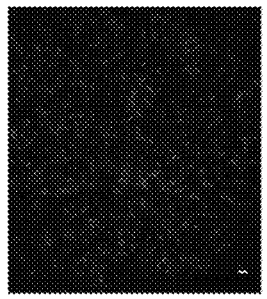
Figure 16F:
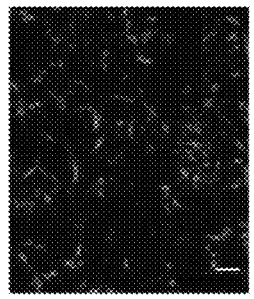
Figure 16G:
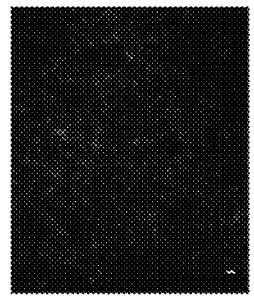
Figure 16H:
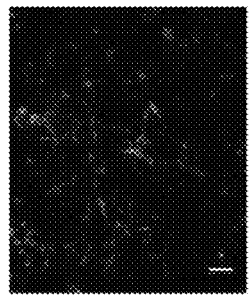
Figure 16I:
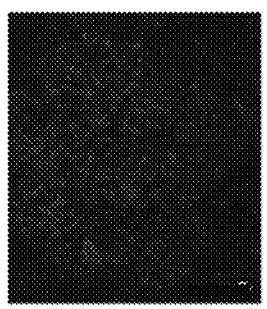
Figure 16J:
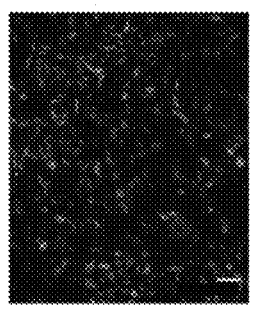
Figure 16K:
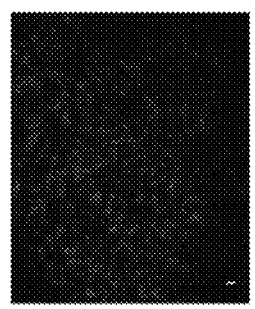
Figure 16L:
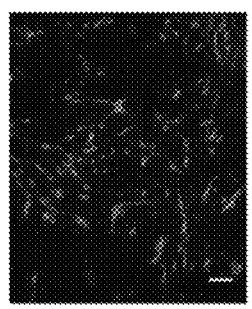
Figure 17A:
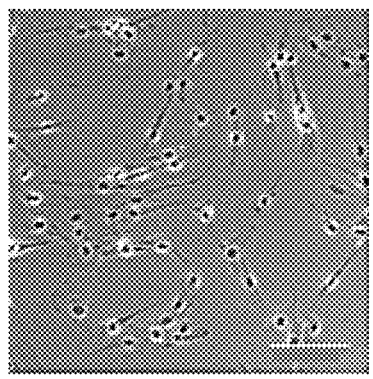
FIGS. 17A-17G demonstrate differentiation of bovine satellite cells (BSC) and formation of myotubes. (A-C) are images of BSC cells before differentiation; (D-F) are images of BSC cells after differentiation. (G) is a vertical bar graph showing the fusion index (FI) of the samples. (A and D) light microscopy; (B and E) Hoechst; and (C and F) Myogenin. The difference in the automatic FI before and after differentiation was found to be statistically significant (P-value=0.00003), while the difference between the automatic and manual FI was not.
Figure 17B:
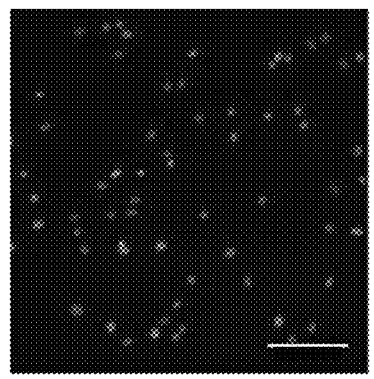
Figure 17C:
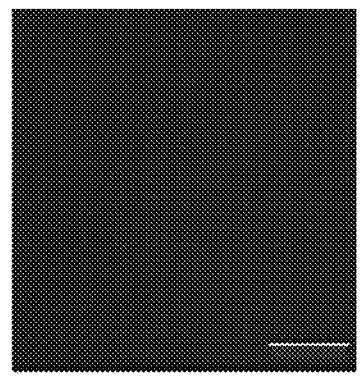
Figure 17D:
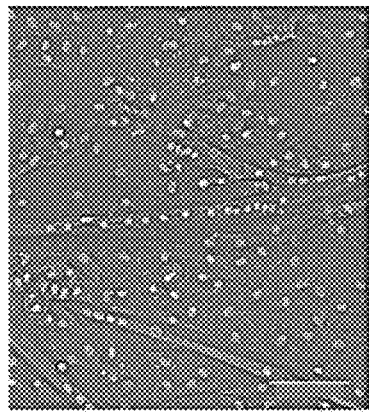
Figure 17E:
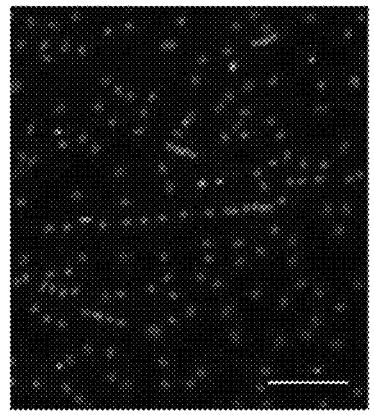
Figure 17F:
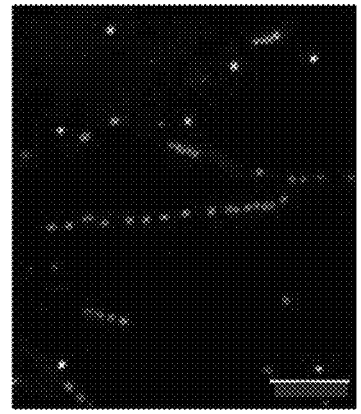
Figure 17G:
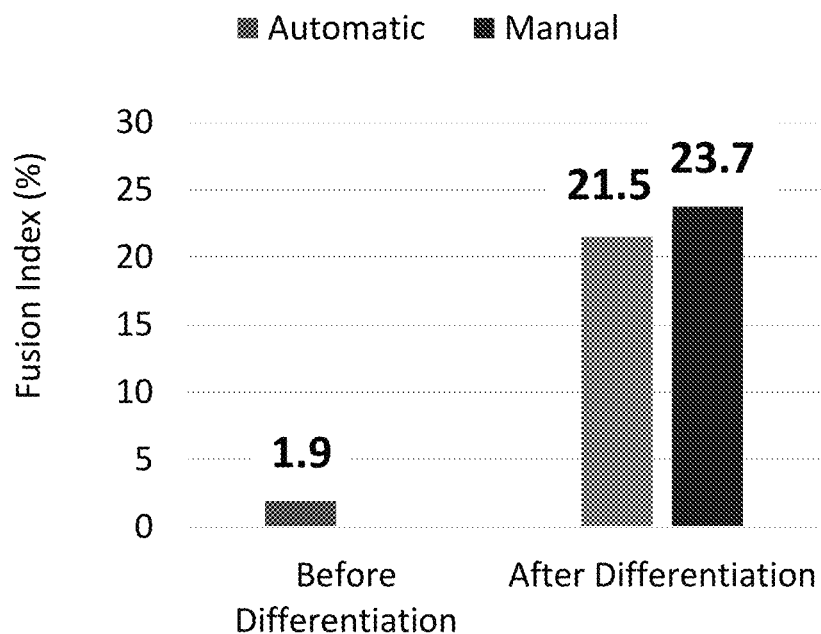

In order to test if bovine endothelial cells (EC; BAEC—Bovine aortic endothelial cells or BSKMVEC—Bovine skeletal muscle microvascular endothelial cells) seeded in co-culture with supporting cells enhance vascularization and scaffold coverage, BAEC were co-seeded with either BDF or BASMC. Indeed, co-culturing fibroblasts together with myoblasts and endothelial cells has been shown to increase vascularization of engineered muscle constructs and promoted stabilization of the vessel structure over time. Cells were found to cover the entire scaffold (FIG. 12). Furthermore, when BAEC were seeded in co-culture with BASMC (FIG. 12A) the inventors noticed that the staining for ECs is reduced over time. Also, a vessel like structure was evident on day 2 in this combination. When BAEC were seeded in co-culture with BDF (FIG. 12B) the inventors noticed no vessel-like structures. When BSKMVEC were seeded in co-culture with BASMC (FIG. 13A) the inventors noticed much more BASMC than BSKMVEC. Also, vessel-like structures were evident with BASMC (FIG. 13A) and with BDF (FIG. 13B), throughout the entire experiment period.

Example 8

Specific Cell Ratio Improves Blood Vessel Network Formation

To further improve vessel networks the inventors seeded bovine BAEC with supporting cells (BDF or BASMC) in different ratios. The inventors examined 3 different ratios that were: 1:3, 1:1 and 5:1 ECs to supporting cells. The inventors clearly observed self-assembly of the BAEC cells (FIGS. 14-16) which created vessels, as early as on day 2 in the presence of BASMC (FIGS. 14 and 16). The inventors also noticed that by day 6 there were less ECs then on day 2 and that the BAEC created a region of vessel network in a 1:1 BAEC to BASMC ratio. BAEC in the presence of BDF seemed not to create vessels (FIG. 15).

Example 9

Bovine Satellite Cell (BSC) Differentiation in a Cell Culture

The inventors then examined myogenin expression before and after myotube formation from BSC, and further assessed the ability to use DAPI-Myogenin for fusion index (FI) measurement. The inventors found little evidence of myogenin expression in undifferentiated BSC (FIG. 17). Myogenin expression occurred mainly in the nuclei of myotubes and in some nuclei around the myotubes. It was shown that the fusion Index (FI) can be calculated automatically by the ratio of myogenin/Hoechst nuclei count, which was found to be comparable to the manual FI calculation. This protocol was further used in quantification of myotube formations.

Example 10

Optimization of BSC Differentiation in a Cell Culture

The inventors then wanted to optimize BSC differentiation in 2D. The inventors checked which growth factors (GFs) can be added during (1) the expansion phase which will not inhibit myotube formation during the differentiation stage and (2) at the end of the differentiation phase which will increase myotube size and FI.

Figure 20H:
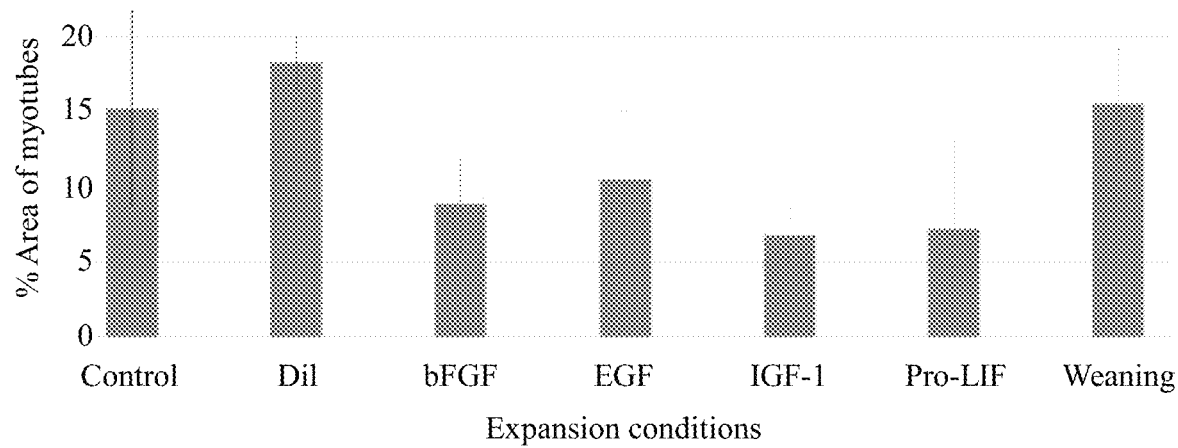

After the expansion phase and before the differentiation phase, spontaneous myotubes appeared in samples that did not contain bFGF (FIG. 18) suggesting bFGF inhibits myotube formation. EGF, IGF-1 and DiI did not seem to affect myotube formation. Increased cell density occurred in IGF-1, Pro-LIF and Weaning. On day 4 of differentiation, the inventors observe an increased in total myotubes under bFGF and Pro-LIF culture conditions. The bFGF maintained the stemness of the BSC and once removed the cells burst into differentiation (FIG. 19). On day 7 of differentiation, the inventors observed a high area of myotube in the control, weaning and DiI, as compared to the other tested conditions (FIG. 20). The inventors concluded that there is a fine line between myotube formation and cell death. Accordingly, cells should be grown in expansion media containing bFGF (alone or with Pro-LIF) until reaching confluency and then be transferred to differentiation media for a short period of time of 2-5 days. Further shown was high abundancy of myotubes when IGF-1 or IGF-1 and EGF were added to the cell culture media.

Example 11

Optimization of BSC Expansion on a Porous Scaffold

Figure 21:
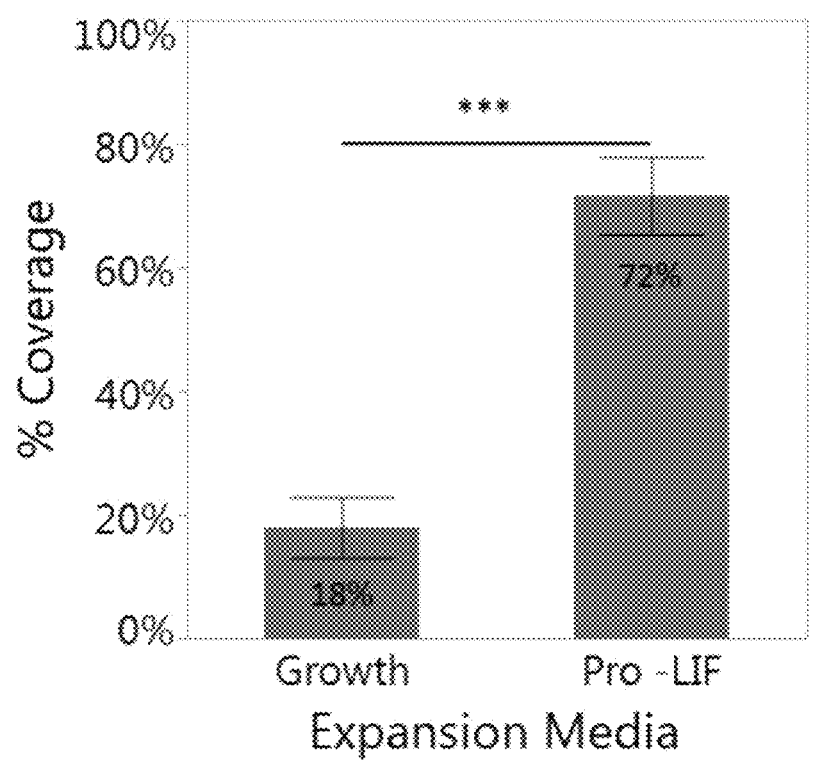
FIG. 21 is a vertical bar graph demonstrating quantification values of cell coverage on porous scaffolds at day 7 with growth media or Pro-LIF media.

The inventors then attempted to increase BSC coverage on the TSP scaffold of above 60% as previous experiments showed low cell coverage on the porous scaffold. Therefore, GFs were added to the expansion phase and initial cell number at seeding was increased. Quantification of the cell coverage area showed that cells cultured with growth media supplemented with GFs (i.e., Pro-LIF) covered 72±15% of the scaffold, while cells cultured solely on growth media covered approximately 18% of the scaffold (FIG. 21). A difference which was found to be statistically significant between the two treatments (P value=0.0009).

Example 12

Optimization of BSC Differentiation on a Porous Scaffold

Figure 22A:
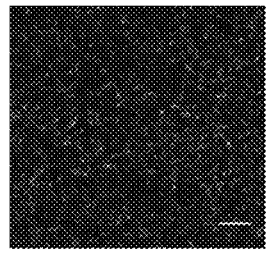
FIGS. 22A-22L are confocal microscopy images of fluorescently labeled BSC differentiated on a porous scaffold. Expansion phase included: (A-D) Cells cultured on growth media; (E-H) Cells cultured on Pro-LIF media; (I-L) Cells cultured on Pro-LIF-bFGF media. Differentiation phase included: (A, E and I) No growth factors (GFs) were added to the differentiation media; (B, F and J) IGF-1 was added to the differentiation media; (C, G and K) EGF was added to the differentiation media; and (D, H and L) IGF-1 and EGF were added to the differentiation media. DiI; Desmin; Scale bar=100 μm.
Figure 22E:
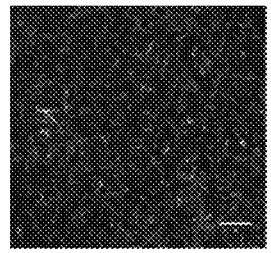
Figure 22I:
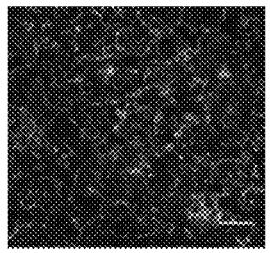
Figure 22B:
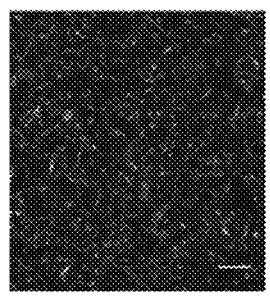
Figure 22F:
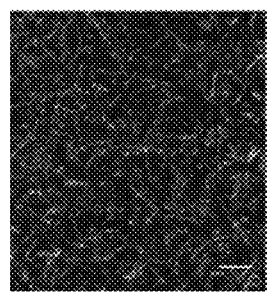
Figure 22J:
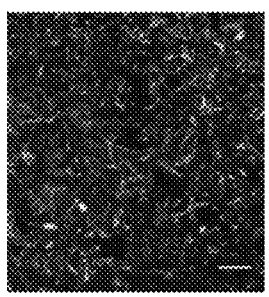
Figure 22C:
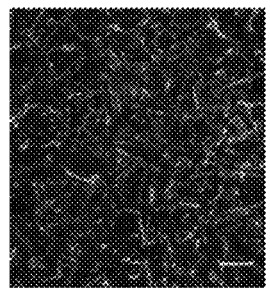
Figure 22G:
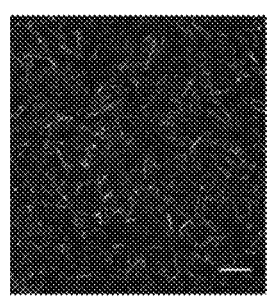
Figure 22K:
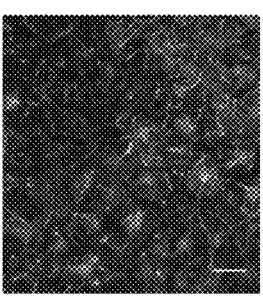
Figure 22D:
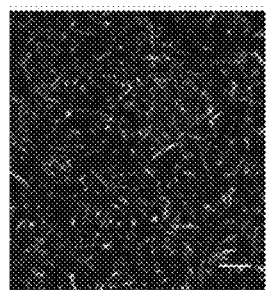
Figure 22H:
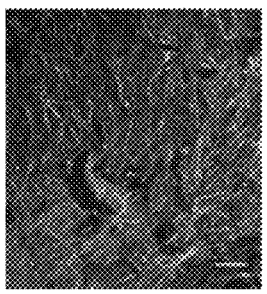
Figure 22L:
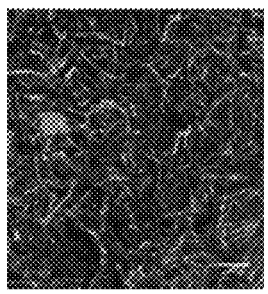
Figure 24C:
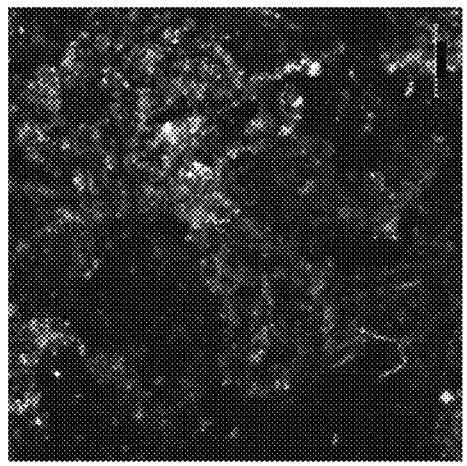
FIGS. 24A-24F are immunofluorescent micrographs of PLLA/PLGA scaffolds 14 days post seeding. BSC, SMC and BEC were seeded on PLLA/PLGA scaffolds in different cellular densities of (A-C) 2:1:1 and (D-F) 2:1:5. (A and D) BSC and SMC (2:1); (B and E) BSC and BEC (2:1); and (C and F) monoculture of BSC alone. Scaffolds were stained for DAPI; Myogenin (gray); DiI; and CD31. Scale Bar of=100 μm.
Figure 24F:
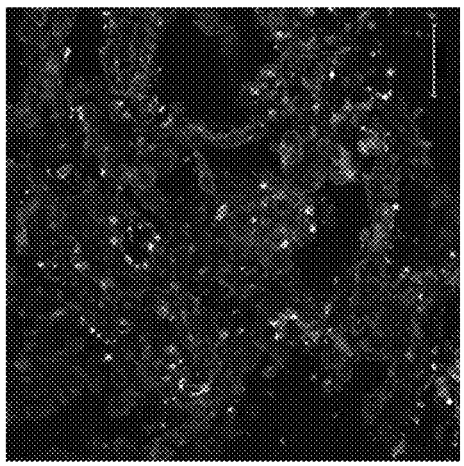
Figure 24B:
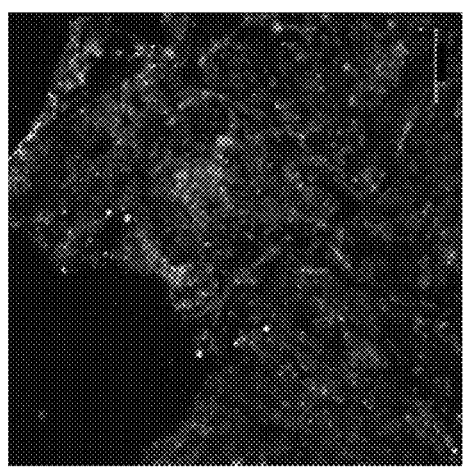
Figure 24E:
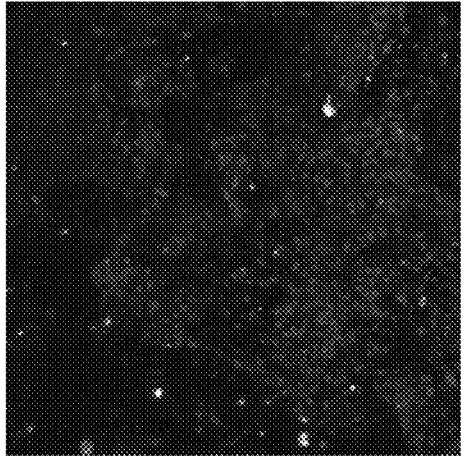
Figure 24A:
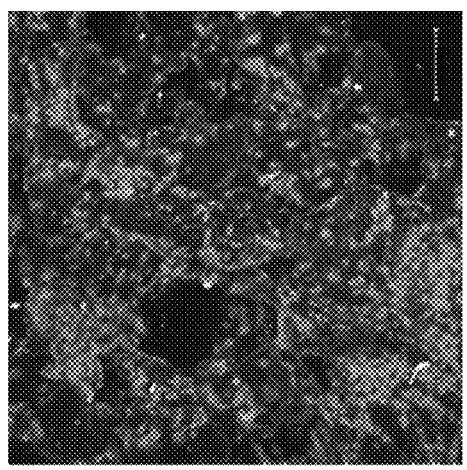
Figure 24D:
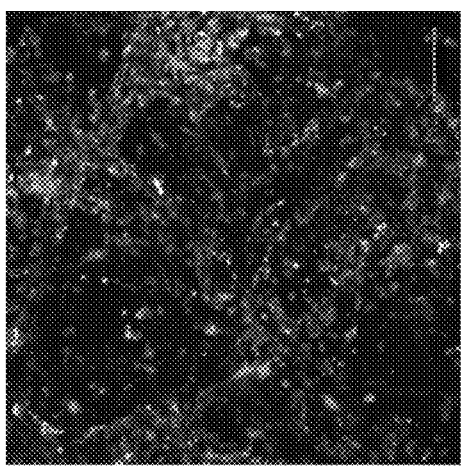
Figures 26A, 26B, 26C, 26D, 26E:
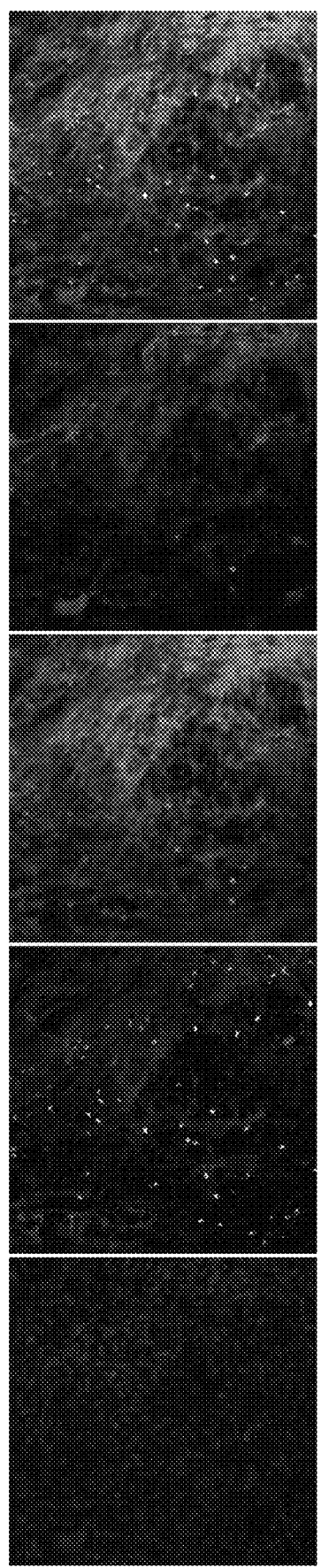
FIGS. 26A-26E are immunofluorescent micrographs of BSC, SMC and BEC tri-cultured on textured soy protein scaffolds, 14 days post seeding. Scaffolds were stained for (A) DAPI; (B) Myogenin; (C) DiI; and (D) CD31. (E) is a merged image of (A-D).

In order to find the optimal conditions for myotube formation on 3D scaffolds, the inventors scanned multiple combinations of expansion media and subsequently differentiation media. The myotubes formed without the GFs in the differentiation media (FIGS. 22A, E and I) were small and rounded. Adding IGF-1 to the differentiation media resulted in myotubes—which were rarely observed in the growth media (FIG. 22B), common in the Pro-LIF-bFGF (FIG. 22J) and abundant in the Pro-LIF media (FIG. 22F). Adding EGF to the differentiation media resulted in myotubes in all expansion media (FIGS. 22C, G and K). Adding IGF-1+EGF resulted in myotubes in the growth media (FIG. 22D) and Pro-LIF-bFGF (FIG. 22L) and abundant myotubes in the Pro-LIF (FIG. 22H).

Example 13

Figure 27B:
FIGS. 27A-27B are micrographs of tri-chrome staining of tri-culture of BSC, SMC and BEC seeded on PLLA/PLGA scaffold at a ratio of 2:1:1, 14 days post seeding. (A) Tile scan of ×5 magnification and (B) a ×10 magnification. Scaffolds were stained to tri-chrome. Positive extracellular matrix (ECM) stains are encircled. Scale bar=100 μm.
Figure 27A:
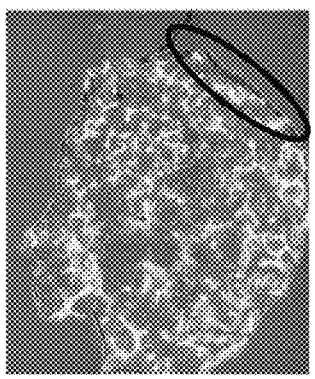

Tri-Culture Increases BSC Proliferation, Elongation, and Coverage on a Porous Scaffold The inventors then wanted to examine the effect of tri-culturing BSC with constant amount of smooth muscle cells (SMC) and different amounts of skeletal microvascular endothelial (SkMVEC) (2:1:1 and 2:1:5, respectively) on BSC survival, proliferation and myotube differentiation (positive for the differentiation marker—Myogenin). The inventors observed that in the low SkMVEC concentration (2:1:1) BSC appeared to be more elongated compared to their appearance when incubated with higher concentration of SkMVEC (2:1:5; FIG. 28). The inventors also observed that BSC had increased their coverage over the porous scaffold and appeared to be more differentiated compared to either monoculture or co-cultures comprising BSC (controls). The inventors concluded that tri-cultures better support BSC proliferation and differentiation compared to the other tested groups in both incubation ratios, and summarized BSC differentiation potential as follows: BSC alone <BSC+EC<BSC+SMC<BSC+EC+SMC (FIGS. 23-26 and 28). The inventors also observed extracellular matrix (ECM) secretion in tri-cultures of BSC+SMC+SkMVEC (2:1:1) (FIGS. 27A-27B).

Example 14

Tri-Culture Increases BSC Differentiation on a Textures Soy Protein Scaffold

Figure 29M:
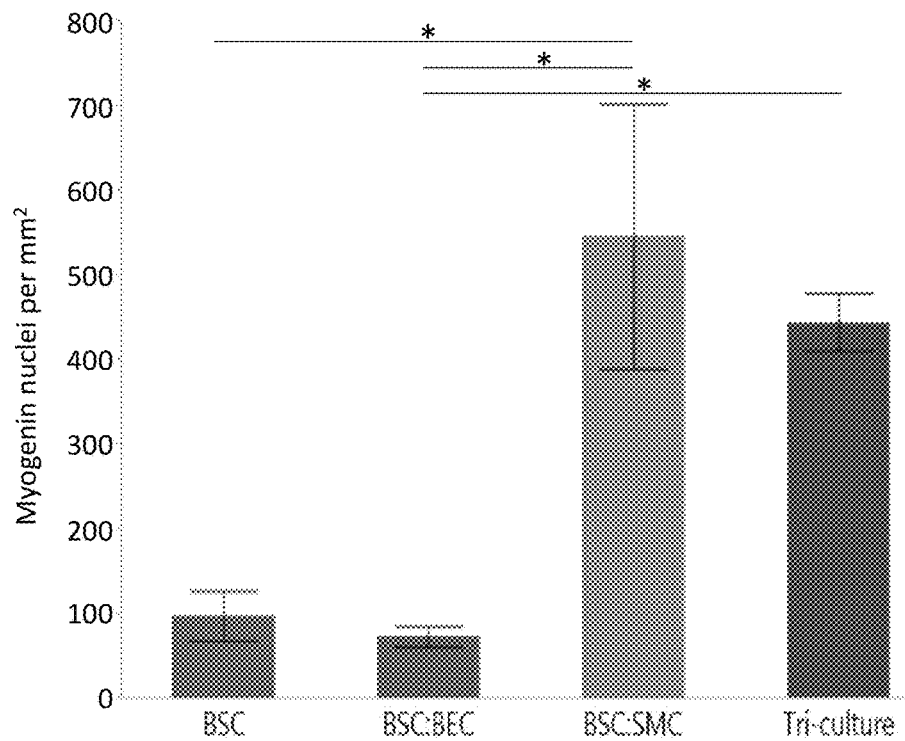
FIGS. 29A-29N describe differentiation of tri-cultures on textured protein scaffolds. (A-L) are fluorescent images of immunostained textured soy protein scaffolds, 14 days post seeding. Cells were seeded on textured soy protein scaffolds (A, E and I) BSC, (B, F and J) BSC+BEC; (C, G and K) BSC+SMC; and (D, H and L) tri-culture of BSC+SMC+BEC. (A-D) ×20 magnification, (E-H) tile scan of ×20 and (I-L) myogenin staining, ×63 magnification. Scaffolds were stained to DAPI (blue), Myogenin (grey), DiI (red) and CD31. Scale bar=100 μm. (M) is a vertical bar graph of myogenin expression quantification on the TSP scaffolds in mono-culture (BSC only), co-cultures (BSC+BEC; or BSC+SMC) and tri-culture (BSC+SMC+BEC). (N) is a vertical bar graph of BSC coverage quantification on the TSP scaffolds in a mono-culture and a co-culture with SMC.
Figure 29N:
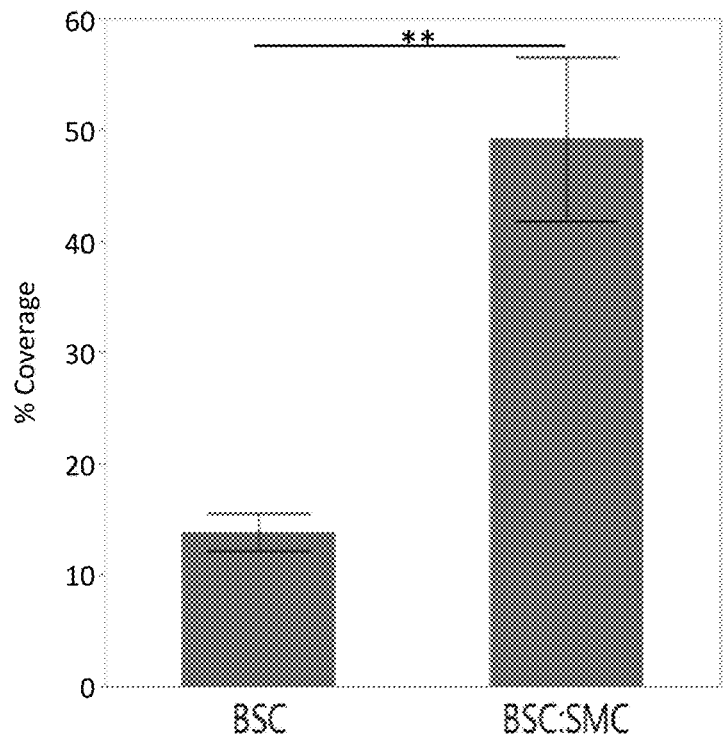

The inventors then wanted to examine the effect of tri-culturing BSC with constant amount of smooth muscle cells (SMC) and skeletal microvascular endothelial (SkMVEC) (2:1:1 respectively) on BSC survival, proliferation and myotube differentiation (positive for the differentiation marker—Myogenin). The inventors observed that not only BSC had increased their coverage over the TSP scaffold when seeded either in co-culture with SMC or in tri-culture with SMC and BEC but also appeared to be more differentiated compared to either monoculture (BSC only) or co-culture (BSC with BEC; FIG. 29).

Example 15

Seeding BSC without the Addition of Solidifying Gel

Figure 30:
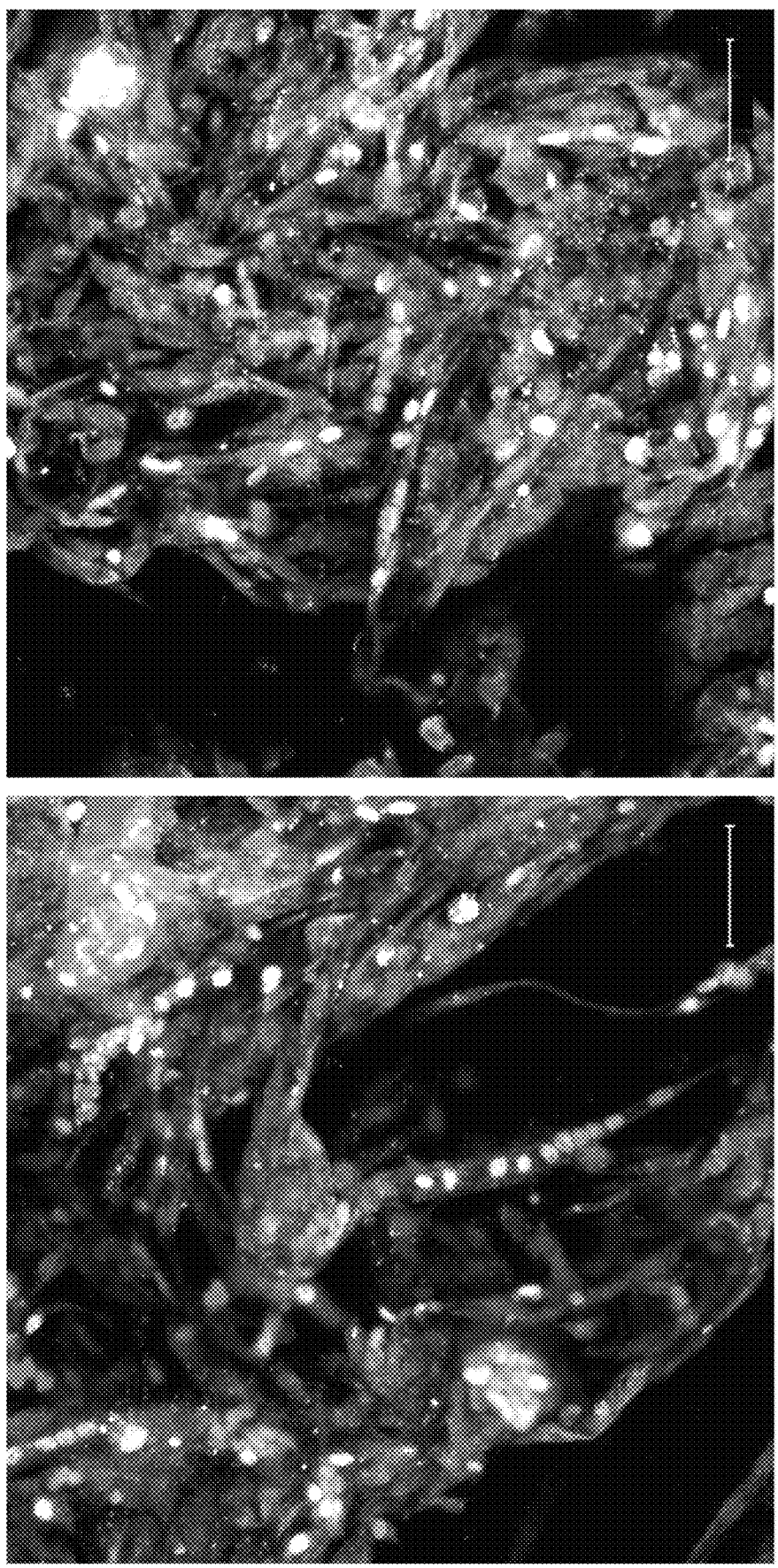
FIG. 30 is fluorescent images of immunostained BSC seeded without gel on Gelfoam scaffolds, 14 days post seeding. Scaffolds were stained to DAPI, Myogenin (grey), DiI; and CD31. Scale bar=50 μm.

The inventors then wanted to examine the effect of seeding BSC on FDA-approved collagen based scaffold (Gelfoam©) without the addition of solidifying agents (e.g., fibrin. The inventors observed successful BSC differentiation, as demonstrated by myotube formation (FIG. 30).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An edible composition comprising:
   a) an edible three-dimensional porous scaffold comprising vegetable protein;
   b) bovine myotubes comprising 10,000-250,000 myotube nuclei per mm$^3$ of said three-dimensional porous scaffold; and
   c) a plurality of bovine cell types, the plurality of bovine cell types comprising:
      (i) myoblasts or satellite cells;
      (ii) at least one type of extracellular matrix (ECM)-secreting cells selected from the group consisting of stromal cells, fibroblasts, pericytes, and smooth muscle cells; and
      (iii) no more than 15% endothelial cells or endothelial progenitor cells thereof.

2. The edible composition of claim 1, wherein said plurality of bovine cell types comprises myoblasts, at least one type of extracellular matrix (ECM)-secreting cells, and endothelial cells or progenitor cells thereof.

3. The edible composition of claim 1, wherein said plurality of bovine cell types comprises satellite cells, ECM-secreting cells, and endothelial cells.

4. The edible composition of claim 1, wherein said ECM-secreting cell is a fibroblast, a progenitor cell thereof, or a combination thereof.

5. The edible composition of claim 1, wherein the vegetable protein is selected from the group consisting of: a textured protein and a non-textured protein.

6. The edible composition of claim 5, wherein said textured protein is textured soy protein.

7. The edible composition of claim 1, wherein said edible three-dimensional porous scaffold comprises pores with an average diameter ranging from 20 to 1,000 micrometers.

8. The edible composition of claim 1, wherein said edible three-dimensional porous scaffold further comprises an extracellular matrix.

9. The edible composition of claim 1, wherein the vegetable protein is at least 50% pure.

10. The edible composition of claim 1, wherein said plurality of bovine cell types comprises satellite cells, smooth muscle cells, and endothelial cells.

11. The method for producing the edible composition of claim 1, the method comprising the steps of:
    a) incubating an edible three-dimensional porous scaffold comprising vegetable protein and a plurality of bovine cell types comprising: myoblasts or satellite cells;
    at least one type of extracellular matrix (ECM)-secreting cells selected from the group consisting of stromal cells, fibroblasts, pericytes, and smooth muscle cells; and no more than 15% endothelial cells or endothelial progenitor cells thereof; and
    b) inducing differentiation of myoblasts or satellite cells into bovine myotubes, thereby producing the edible composition.

12. The method of claim 11, wherein said plurality of bovine cell types comprises myoblasts, at least one type of extracellular matrix (ECM)-secreting cells, and endothelial cells or progenitor cells thereof.

13. The method of claim 11, wherein said plurality of bovine cell types comprises satellite cells, ECM-secreting cells, and endothelial cells.

14. The method of claim 11, wherein said myoblasts or progenitor satellite cells and ECM-secreting cells are incubated at a ratio ranging between 10:1 to 1:1.

15. The method of claim 11, wherein said ECM-secreting cells and endothelial cells are incubated at a ratio ranging between 1:10 to 1:1.

16. The method of claim 11, wherein said myoblasts or satellite cells and said edible three-dimensional porous scaffold are incubated at a ratio ranging from 10$^3$ to 10$^7$ of said myoblasts or satellite cells to 10 mg of said edible three-dimensional porous scaffold.

17. The method of claim 11, wherein said plurality of cell types comprises satellite cells, smooth muscle cells, and endothelial cells.

18. The method of claim 17, wherein the satellite cells, smooth muscle cells, and endothelial cells are incubated at a ratio of 2:1:1.

* * * * *